US009468956B2

(12) United States Patent
Simundic et al.

(10) Patent No.: US 9,468,956 B2
(45) Date of Patent: Oct. 18, 2016

(54) CLEANING AND DISINFECTING APPARATUS FOR TREATING CONTAINERS FOR HUMAN EXCRETIONS

(71) Applicant: MEIKO Maschinenbau GmbH & Co. KG, Offenburg (DE)

(72) Inventors: Marijan Simundic, Ohlsbach (DE); Ingo Wiegand, Bühlertal (DE); Thomas Peukert, Bühl (DE)

(73) Assignee: MEIKO Maschinenbau GmbH & Co. KG, Offenburg (DE)

( * ) Notice: Subject to any disclaimer, the term of this patent is extended or adjusted under 35 U.S.C. 154(b) by 202 days.

(21) Appl. No.: 14/206,926

(22) Filed: Mar. 12, 2014

(65) Prior Publication Data

US 2014/0190519 A1    Jul. 10, 2014

Related U.S. Application Data

(63) Continuation of application No. PCT/EP2012/067621, filed on Sep. 10, 2012.

(30) Foreign Application Priority Data

Sep. 14, 2011  (DE) ........................ 10 2011 082 654

(51) Int. Cl.
*B08B 9/08*    (2006.01)
*A61G 9/02*    (2006.01)
(Continued)

(52) U.S. Cl.
CPC . *B08B 9/08* (2013.01); *A61G 9/02* (2013.01); *A61L 2/24* (2013.01); *A47L 15/4223* (2013.01); *A61L 2202/24* (2013.01)

(58) Field of Classification Search
None
See application file for complete search history.

(56) References Cited

U.S. PATENT DOCUMENTS 4,527,843 A * 7/1985 Murdoch ................. A61G 9/02
                                                        312/31.2
5,240,686 A * 8/1993 Harlegard ................. A61L 2/07
                                                        134/152
(Continued)

FOREIGN PATENT DOCUMENTS

DE          36 28 793 A1      3/1988
DE         100 48 081 A1      4/2002
(Continued)

OTHER PUBLICATIONS

International Preliminary Report on Patentability, PCT/EP2012/067621, May 30, 2014.

*Primary Examiner* — Michael Barr
*Assistant Examiner* — Cristi Tate-Sims
(74) *Attorney, Agent, or Firm* — Bose McKinney & Evans LLP

(57) ABSTRACT

A cleaning and disinfecting apparatus for treating at least one container for human excretions. The cleaning and disinfecting apparatus comprises at least one cleaning chamber with at least one fluid device for applying at least one cleaning fluid to the container. The cleaning and disinfecting apparatus is configured to carry out at least one cleaning program, wherein, in the cleaning program, the container is emptied and the cleaning fluid is applied thereto. The cleaning and disinfecting apparatus furthermore has at least one image detector. The image detector is configured to identify at least one property of the container. The cleaning and disinfecting apparatus is configured to influence the cleaning program in accordance with the identified property.

22 Claims, 2 Drawing Sheets

(51) Int. Cl.
*A61L 2/24* (2006.01)
*A47L 15/42* (2006.01)

(56) References Cited

U.S. PATENT DOCUMENTS

| | | | | |
|---|---|---|---|---|
| 7,731,154 | B2* | 6/2010 | Parsons | E03D 5/105 |
| | | | | 251/129.04 |
| 8,509,473 | B2* | 8/2013 | Wagner | D06F 9/003 |
| | | | | 382/100 |
| 2002/0020435 | A1 | 2/2002 | Varpio | |
| 2005/0011544 | A1 | 1/2005 | Rosenbauer et al. | |
| 2006/0213543 | A1 | 9/2006 | Litterst et al. | |
| 2006/0219261 | A1* | 10/2006 | Lin | A61B 1/00057 |
| | | | | 134/18 |
| 2007/0044439 | A1* | 3/2007 | Dunn | A61L 2/18 |
| | | | | 55/385.1 |
| 2007/0104608 | A1 | 5/2007 | Gaus et al. | |
| 2010/0186156 | A1* | 7/2010 | Ophardt | E03D 9/00 |
| | | | | 4/301 |
| 2011/0017235 | A1 | 1/2011 | Berner et al. | |
| 2012/0060875 | A1 | 3/2012 | Fauth et al. | |
| 2012/0138092 | A1 | 6/2012 | Ashrafzadeh et al. | |
| 2014/0352745 | A1* | 12/2014 | Wiegand | A61G 9/02 |
| | | | | 134/57 R |

FOREIGN PATENT DOCUMENTS

| | | | | |
|---|---|---|---|---|
| DE | 10048081 | A1 * | 4/2002 | A47L 15/0021 |
| DE | 101 62 505 | A1 | 7/2003 | |
| DE | 103 48 344 | A1 | 5/2005 | |
| DE | 10 2005 014 353 | A1 | 9/2006 | |
| DE | 10 2008 017 597 | A1 | 10/2009 | |
| DE | 10 2009 023 252 | A1 | 12/2010 | |
| EP | 1 192 893 | A2 | 4/2002 | |
| EP | 1 704 809 | A2 | 9/2006 | |
| EP | 2 425 805 | A1 | 3/2012 | |
| WO | WO 2011/048575 | A2 | 4/2011 | |

* cited by examiner

CLEANING AND DISINFECTING APPARATUS FOR TREATING CONTAINERS FOR HUMAN EXCRETIONS

RELATED APPLICATIONS

This application claims priority to DE 10 2011 082 654.8, filed Sep. 14, 2011, and PCT/EP2012/067621, filed Sep. 10, 2012, both of which are hereby incorporated herein by reference in their entireties.

BACKGROUND

The invention relates to a cleaning and disinfecting apparatus, as well as a method, for treating at least one container for human excretions. By way of example, such cleaning and disinfecting apparatuses and methods are used in the hospital or care sector in order to clean containers such as, e.g., bedpans, urine flasks, chamber pots, kidney dishes, washing bowls or other containers which are suitable for holding human or animal excretions, in particular with a volume of at least 100 ml, for example 100-500 ml.

A multiplicity of cleaning apparatuses and cleaning methods for treating containers for human excretions are known. The containers to be cleaned can contain relatively large amounts of liquid or amounts of solid waste, which usually have to be disposed of during the cleaning. Hence, conventional washers are generally not suitable for cleaning such containers. Moreover, such containers can contain infectious wastes or be contaminated in a different way such that disinfection is usually also required in addition to emptying. Such cleaning apparatuses for treating containers for human excretions are accordingly often also referred to as cleaning and disinfecting apparatuses (RDGs). In addition to the aforementioned containers, these are, in principle, also suitable for cleaning other medical objects, as are used, for example, in hospitals or care institutions. However, the goods to be cleaned usually consist of urine flasks, bedpans, kidney dishes, washing bowls or similar containers, the cleaning of which can entail the disposal of relatively large amounts of waste.

An example of a cleaning and disinfecting apparatus is disclosed in DE 103 48 344 A1. In principle, reference can be made to the design of this cleaning and disinfecting apparatus in an exemplary manner in connection with this disclosure, wherein the depicted cleaning and disinfecting apparatus can be complemented according to this disclosure. However, in principle, other designs are also possible. The cleaning and disinfecting apparatus described in DE 103 48 344 A1 contains a device for re-cooling goods to be cleaned. Here, the goods to be cleaned are rinsed within a chamber, which is followed by a pre-cleaning washing step. The cleaning of goods to be cleaned contained in the chamber is then completed using water containing a rinse-aid addition, prior to a step of disinfecting the goods to be cleaned in the chamber by introducing steam into this chamber. Air is forced into the chamber filled with steam when the door is closed, as result of which precipitation of steam within the chamber and cooling and drying of the goods to be cleaned contained in the chamber are brought about.

Thus, a program usually runs in a cleaning and disinfecting apparatus for treating the goods to be cleaned, which program is usually stored in a control of the apparatus. After loading the RDG, a user usually selects a cleaning program and starts the latter, conventionally by actuating a corresponding pushbutton, for example on a membrane keyboard. Here, the user must generally make a subjective decision as to what kind and/or degree of soiling are present on the objects to be cleaned.

In principle, the field of dishwasher technology has disclosed dishwashers which identify the load of the dishwasher. By way of example, DE 10 2009 023 252 A1 describes a dishwasher which has a dish recording means for recording the dishes introduced into the washing container. DE 100 48 081 A1 describes a method for identifying the load of goods to be washed and/or a degree of soiling of the goods to be washed in a program-controlled dishwasher. DE 10 2005 014 353 A1 describes a conveyor washer with a sensor device for goods to be washed for detecting empty compartments in a plurality of compartments of a conveying device. US 2002/0020435 A1 describes a conveyor dishwasher with a plurality of identification sensors for identifying different types of goods to be washed in the conveyor dishwasher.

EP 2 425 805 A1, published after the priority date of the present application, has disclosed a method for cleaning goods to be washed, in particular bedpans, urine flasks or the like. Here, use is made of a program-controlled washing means, which identifies loading of the washing means with goods to be washed. A cleaning program is selected depending on the detected load state. By way of example, the load state of the washing means is captured using an optical detection means. Infrared light-emitting diodes and infrared sensors are described as an example of an optical detection means, by means of which a so-called light curtain is formed.

DE 10 2008 017 597 A1 describes a dishwasher in the form of a program automaton. Here, a detection device for the goods to be washed is used, by means of which the kind of the goods to be washed, which are to be treated, is recorded. A program control means is designed to select automatically a treatment program which is or can be set in advance, depending on the recorded kind of the goods to be washed, which are to be treated. By way of example, the detector means can comprise a camera.

WO 2011/048575 A2 likewise discloses methods and devices for cleaning objects. Here, inter alia, a system is described, which records images of the goods to be cleaned by means of a camera, with a control of the system accordingly selecting a program.

EP 1 192 893 A2 discloses a method for identifying the load of a program-controlled dishwasher with goods to be washed. While the goods to be washed are introduced, inter alia, a profile of light interruptions in a light curtain are recorded and the size and/or the kind of the goods to be washed is deduced therefrom such that a subsequent washing program can be modified or selected in a targeted manner.

DE 101 62 505 A1 discloses a device for washing goods to be washed in a dishwasher. In the process, use is made of at least two spraying means for specific regions of a dish rack and these are actuated individually.

In general, optical sensors, in particular cameras, have previously not been conventional in the field of cleaning and disinfecting apparatuses. Nevertheless, the above-described problem of identifying the kind and degree of soiling when cleaning containers for holding human excretions is significantly more severe in this field compared to dishwasher technology due to the different boundary conditions.

This is due, in particular, to the fact that the containers, as described above, can hold relatively large amounts of waste, for example several 100 ml, which have to be disposed of. Furthermore, as described above, infectious contamination may occur, or else contamination which has very tough deposit buildups. By way of example, a distinction has to be made whether a bedpan is merely filled with urine or whether the bedpan is soiled with balm residues in addition to the human excretions. The latter can require the selection of a specific program, for example with the addition of a balm cleaner. Furthermore, the user must generally make a decision as to what program is selected dependent on the type of vessel. By way of example, loading with merely urine flasks can require the selection of a specific program.

Practice in hospitals and geriatric care institutions usually discloses keyboards which are simple to operate, which typically merely offer few selection options. By way of example, it is possible to select programs for light, average or strong contamination. Furthermore, embodiments are also known in which the program has already been pre-selected and in which the program starts, e.g., automatically after closing the door to the cleaning chamber. The door is generally closed manually or else automatically, for example by activation of a contactless sensor, a pushbutton or a foot pedal.

Known cleaning and disinfecting apparatuses therefore have a number of technical challenges or even disadvantages in practice. Thus, wrong decisions may occur, in particular as a result of the manual program selection which is influenced by subjectivity, which can then, for example, result in insufficient cleaning and/or disinfection of the containers. This incorrect operation can lead to an increased risk of infection. On the other hand, in order to avoid such incorrect operation, the user may be tempted in practice always to select the strongest program in order to obtain a good cleaning and disinfecting result in any case. However, in practice this causes in many cases an unnecessarily high use of resources such as, e.g., water, electricity and possibly process chemicals. Furthermore, strong cleaning programs also require longer program running times, which may lead to capacity bottlenecks in the respective operating unit, for example a care station, if the wrong program is continuously selected.

A further disadvantage of known apparatuses and methods can, in particular, consist of the risk of introducing containers into the cleaning and disinfecting apparatus for which the apparatus has not been designed. This can also lead to insufficient cleaning and/or disinfection. If containers for which the cleaning and disinfecting apparatus has not been designed are introduced into the latter, there can furthermore be malfunctions or even damage. Thus, for example, the containers could jam in the apparatus or fall into an outflow opening of a cleaning chamber. Both cases can lead to malfunctions or else to damage to the apparatus.

SUMMARY

The present invention provides a cleaning and disinfecting apparatus and a method for treating at least one container for human excretions, which at least largely avoids the disadvantages of known cleaning apparatuses and methods. In particular, the cleaning apparatus and the method can react flexibly to different kinds of containers and/or soiling and at least largely avoid incorrect operations, while at the same time having a high quality cleaning result.

In one embodiment, the cleaning and disinfecting apparatus can be configured to carry out a method according to this disclosure in which the cleaning and disinfecting apparatus can, for example, have an appropriate control. The method can be carried out using the cleaning and disinfecting apparatus according to this disclosure. Accordingly, reference can be made to the description of optional details of the method for the description of possible details of the cleaning and disinfecting apparatus, and vice versa.

Furthermore, reference is made to the fact that the terms "to have" and "to comprise," as well as corresponding grammatical variations of these verbs, are used in the non-exclusive sense below. Thus, the situation "A has B" or the situation "A comprises B" describe the option of A exclusively consisting of B or else, alternatively, the situation that A, in addition to B, contains one or more further components and/or constituents. Furthermore, when a structural element is introduced with the indefinite articles "a" or "an," it should be understood unless otherwise specified that these indefinite articles can be read as including "at least one" or "one or more."

According to a first aspect of this disclosure, a cleaning and disinfecting apparatus for treating at least one container for human excretions is proposed. By way of example, this cleaning and disinfecting apparatus can be embodied in accordance with the above-described known system, with the additional features according to this disclosure described below. However, a different embodiment is also possible. Here, in general, a treatment is understood to mean cleaning which, as will still be described in more detail below, contains an application of at least one cleaning fluid to the container. In particular, the cleaning can be configured such that it at least largely frees the container from deposited contamination. Furthermore, in addition to cleaning, the treatment also contains disinfection. In general, within the scope of this disclosure, disinfection is understood to mean a reduction in germs. This reduction in germs can, for example, be brought about by a thermal treatment and/or a chemical treatment of the at least one container, for example by a treatment using a disinfecting gas and/or using hot steam. The disinfection can optionally lead right up to the sterilization of the container. Hence, within the scope of this disclosure, a cleaning and disinfecting apparatus for treating at least one container for human excretions is to be understood to mean a device which is configured to carry out a treatment of the container, containing at least one clean and at least one disinfection. The at least one clean and the at least one disinfection can, for example, occur in separate program steps of a program sequence. By way of example, the method and/or the cleaning and disinfecting apparatus can comprise a support a program, in which at least one cleaning step and at least one disinfection step are provided as separate program steps.

In general, a container for human excretions is understood to mean a container which has at least one holding region, for example a cavity or recess, in which a relatively large amount of human or else animal excretions can be held, for example an amount of at least 50 ml, in particular at least 100 ml, preferably at least 200 ml or even at least 500 ml. In addition to the at least one holding region, for example the at least one cavity, the container can furthermore have at least one opening. This opening can be present from the outset and/or it can also be created at a later time. Furthermore, at least one opening can also be created during and/or prior to the treatment, for example by mechanical opening of the container and/or by cutting and/or ripping open the container, for example within the scope of the proposed method. Furthermore, the opening can be configured to be opened and/or closed in a reversible or irreversible manner. The container can have at least one container wall, which may have a rigid or else deformable design, in particular a flexible design. Thus, for example, the container can have a vessel with a rigid container wall, for example made of one or more of the following materials: glass, plastics, ceramics and metal. Alternatively, or in addition thereto, the container can also have at least one deformable container wall, for example at least one film bag, in particular a film bag made of a polymer material. Thus, the container for human excretions can, for example, be wholly or partly configured as an initially closed container in the form of a film bag.

In addition to at least one clean and at least one disinfection, the treatment can, in particular, also contain an emptying of the container, for example prior to the application of the cleaning fluid. To this end, the cleaning and disinfecting apparatus can, for example, have one or more disposal devices, which are configured to receive and dispose of the aforementioned amounts of human excretions. By way of example, as will still be explained in more detail below, the cleaning and disinfecting device can comprise an outflow in the cleaning chamber, for example an outflow with a cross section of at least 30 mm, in particular of at least 50 mm, particularly preferably of at least 70 mm or even at least 100 mm. This outflow can, as will still be explained in more detail below, be connected to, e.g., a siphon bend. By way of example, if the container comprises at least one film bag, the cleaning and disinfecting apparatus can, in particular, be configured to open, for example cut and/or rip open, the film bag prior to and/or during the treatment by means of an appropriate device such that said film bag can be emptied. By way of example, this device can be fixedly integrated in the cleaning and disinfecting apparatus and/or can, according to requirements, be inserted into the cleaning and disinfecting apparatus by the user.

The cleaning and disinfection apparatus can be configured to treat simultaneously precisely one container or a plurality of containers in each case. In particular, the at least one container can be selected from the group consisting of: a urine flask, a bedpan, a kidney dish, a wash bowl, a chamber pot, a urine collection bag, a secretion bag. A combination of the aforementioned containers and/or other containers is also feasible.

The cleaning and disinfection apparatus comprises at least one cleaning chamber with at least one fluid device for applying at least one cleaning fluid to the container. Here, a cleaning chamber is understood to mean a completely or partly closed chamber, into which the container can be introduced and in which the treatment or part of the treatment of the container occurs. In particular, the cleaning and disinfecting apparatus can be embodied as single-chamber cleaning apparatus, with all treatment steps occurring in the same cleaning chamber. Hence, the cleaning fluid can be applied in the cleaning chamber, and the disinfection of the container and/or an emptying of the container can optionally occur there. By way of example, the cleaning and disinfecting apparatus can be configured to initially undertake an emptying of the container, for example into an outflow, in at least one cleaning program, whereupon the at least one cleaning fluid is applied, wherein it is also possible to apply a plurality of cleaning fluids in succession, whereupon disinfection can occur, for example disinfection using hot steam and/or chemical disinfection by means of at least one chemical disinfection agent such as, for example, by means of at least one liquid disinfection agent and/or by means of at least one germ-killing gas such as, e.g., ethylene oxide. In particular, the cleaning chamber can be closed completely and can, for example, as explained below, have at least one door.

In general, within the scope of this disclosure, a cleaning fluid is to be understood to mean a liquid and/or a gas which has a cleaning effect on the container, for example by virtue of the cleaning fluid causing deposited contamination to be washed from at least one surface of the container. The cleaning fluid can, in particular, be an aqueous cleaning fluid, wherein water can be used, optionally with addition of one or more cleaning agents and/or additives and/or disinfection agents. In principle, such cleaning fluids are known from the prior art. By way of example, the cleaning and disinfecting apparatus can have at least one tank, by means of which the cleaning fluid can be provided to the fluid device. Alternatively, or in addition thereto, the cleaning and disinfecting apparatus can also have one or more connectors for providing the cleaning fluid, for example a freshwater connector and/or a hot-water connector, which can, for example, be connected to a building-side supply. Furthermore, as will still be explained in more detail below, the cleaning and disinfecting apparatus can also have, e.g., one or more steam generators, for applying hot steam onto the container. Furthermore, the cleaning and disinfecting apparatus can also have one or more metering tanks, in which additives of the cleaning fluid can be stored, for example by virtue of these being mixed in a metered fashion to other components of the cleaning fluid, for example by metered mixing into water. By way of example, one or more cleaner tanks and/or one or more tanks for additives and/or one or more tanks for disinfection agent can be comprised in the cleaning and disinfecting apparatus and/or on the cleaning and disinfecting apparatus.

In general, a fluid device is to be understood to mean a device which is configured to apply the at least one cleaning fluid to the container. By way of example, there can be application by spraying and/or dripping and/or radiating the cleaning fluid onto the container. In particular, the fluid device can have at least one nozzle, which generates at least one fluid beam that impacts on the container. By way of example, the fluid device can comprise at least one nozzle, which sprays and/or radiates one or more beams of the cleaning fluid onto the container from one or more spatial directions in a targeted manner.

The cleaning and disinfecting apparatus is configured to carry out at least one cleaning program. To this end, the cleaning and disinfecting apparatus can, for example, comprise at least one control. This control can have a centralized or decentralized embodiment and/or can, for example, comprise at least one data processing device, which is configured by program-technical means to control the cleaning program. By way of example, the data processing device can be configured to set one, some or all program parameters of the cleaning program, for example in a specified sequence and/or with a specified timeframe.

The cleaning and disinfecting apparatus can therefore have at least one control. This control can, in particular, comprise one or more data processing devices. The at least one control can have a centralized and/or integral design or can else have a decentralized design and comprise several control components. By way of example, the control can comprise one or more processors, which can optionally be connected to one another in a wireless or wired manner in order to interchange information and/or commands. The at least one control, for example the at least one optional data processing device, can, in general, be wholly or partly integrated into a common module with the at least one cleaning chamber, for example in a common housing. Alternatively, or in addition thereto, the at least one control, for example the at least one data processing device, can also be arranged wholly or partly outside of a module of the cleaning and disinfecting apparatus comprising the cleaning chamber, for example outside of a housing surrounding the cleaning device, for example as an external control.

The at least one control can comprise one or more control components, for example a plurality of data processing devices which, for example, can be connected to one another by at least one interface and/or by at least one data connection, for example for interchanging data and/or general information and/or control commands. In general, the control can also wholly or partly comprise at least one data processing device, which, in addition to a control of the cleaning and disinfecting apparatus, serves for at least one further purpose, for example a PC.

In general, the optional control can therefore comprise one or more control components, which in each case can be wholly or partly realized as hardware components and/or can be wholly or partly realized as software components.

If a plurality of control components are provided, these can be embodied as different hardware components, which can be arranged in a spatially separated manner, for example in the form of a plurality of data processing devices. Alternatively, or in addition thereto, the control can comprise a plurality of control components, which can be implemented as software components in one and the same hardware, for example in one and the same data processing device.

If a plurality of control components are provided, these can be arranged together in one location or else in a spatially separate manner. The control components can be configured without a connection to one another and/or can be connected to one another in pairs or in groups in a wired and/or wireless manner in order to interchange unidirectional commands and/or data, for example commands of the cleaning program and/or image data of at least one image of the container recorded by the image detector.

If provision is made for a plurality of control components, these can in each case also be configured for carrying out different functions. By way of example, provision can be made for at least one control component in the form of a cleaning program control, wherein the cleaning program control is configured to wholly or partly control the sequence of the cleaning program. Furthermore, by way of example, it is alternatively, or in addition thereto, possible to provide at least one control component in the form of an image processing control. This image processing control can, for example, comprise a data processing device or part of a data processing device, which is configured by program-technical means to store an image and/or to process an image.

Within the scope of this disclosure, image processing can, in general terms, be understood to mean a process in which image data are subjected to at least one operation which modifies the image data. This operation, which can, in particular, be a calculation operation, can, for example, comprise at least one operation selected from: filtering, smoothing, a data reduction, brightening, darkening, changing the contrast. Other operations, such as, e.g., the comparison of several images within an image sequence, can, in principle, also be employed, additionally or as an alternative thereto, and, in principle, are known to a person skilled in the art of image processing.

If the control comprises at least one control component in the form of an image processing control, for example in addition to at least one control component in the form of a cleaning program control, these control components can, in particular, have such a spatially separate design that at least one control component has an external design, for example in an external computer, in particular an external PC, which then wholly or partly forms a component of the control. In general, external can be understood to mean an embodiment in which the component referred to as external is formed in one or more modules, which are arranged spatially separated from a module of the cleaning and disinfecting apparatus comprising the cleaning chamber.

If the control has at least one control component in the form of at least one image processing control, then the image processing control can have a wholly or partly separated design from the image detector, for example with spatial separation, wherein, however, at least one data connection preferably exists between the image detector and the image processing control, which data connection can be wired and/or wireless. Thus, for example, an external computer, for example an external PC, can be employed for complete or partial display and/or storing and/or processing of image data. Alternatively, or in addition thereto, the at least one image processing control can also be wholly or partly integrated into the at least one image detector and/or be spatially combined with the image detector. Thus, for example, use can be made of a camera with an integrated data processing device, for example an integrated processor. The processor can be configured by program-technical means to undertake data processing and/or pre-processing of the image detector data, for example of image data of at least one image of the container, for example image processing and, in particular, data reduction.

In general, a cleaning program is to be understood to be a temporal sequence of a cleaning of the container defined by one or more cleaning program parameters. Such cleaning program parameters can, for example, comprise one or more cleaning program parameters selected from the group consisting of: at least one duration of an application of the cleaning fluid to the container; a kind and/or composition of the cleaning fluid; an intensity of the application of the cleaning fluid, for example a pressure of the cleaning fluid; a temperature of the cleaning fluid; a temperature in the cleaning chamber; a duration of an individual cleaning program step; a sequence of different cleaning program steps; an application onto the goods to be cleaned from different nozzles; an application onto the goods to be cleaned from nozzles which change in position, for example lift/rotation nozzles. In particular, the cleaning program can have at least one cleaning program step. In general, a cleaning program step is understood to mean a defined portion of the cleaning program which, for example, is distinguished by uniform cleaning program parameters. By way of example, the cleaning program can comprise a plurality of such cleaning program steps. By way of example, the cleaning program can comprise an emptying step and/or a washing step, in which one or more cleaning fluids are applied, and/or a disinfection step, in which there is, for example, disinfection using hot steam and/or other disinfection means. In principle, other cleaning program steps are also possible. By way of example, the cleaning program can have a sequence of cleaning program steps, wherein the sequence of the individual cleaning program steps and/or the duration of the individual cleaning program steps and/or the composition of the cleaning program as such can also be considered to be cleaning program parameters.

In the cleaning program, as explained above, the container is emptied, for example into at least one outflow, and the cleaning fluid is applied thereto. In particular, the container can be emptied automatically. By way of example, the container can already be emptied when loading the container into the cleaning and disinfecting apparatus, for example by virtue of the container being tilted and/or pivoted during loading, wherein the content of the container can, for example, be emptied into an outflow. The introduction of the container into the cleaning and disinfecting apparatus and/or the closing of the cleaning and disinfecting apparatus can thus be considered to be already part of the cleaning program. Here, in general, emptying is to be understood to mean a process in which the container is moved from a transport position, in which the content remains in the container, into at least one emptying position, in which a possible content of the container can flow out of the container provided this content has a suitable consistency. In particular, this can occur under the influence of its own weight and/or under the influence of centrifugal forces on the content. By way of example, the container can be pivoted and/or tilted in such a way that at least one opening of the container points downward in such a way that the content can flow out, for example into the optional outflow. Furthermore the cleaning fluid is applied to the container in the cleaning program, as described above, for example in one or more washing steps. Here, there can also be a sequence of a plurality of cleaning steps, for example by virtue of different kinds of cleaning fluids being applied in sequence.

The cleaning and disinfecting apparatus furthermore has at least one image detector. Within the scope of this disclosure, an image detector should, in general, be understood to mean a device which is configured to record at least one spatially resolved optical signal. By way of example, the image detector can comprise a plurality of optically sensitive elements, in particular optically sensitive semiconductor components, arranged in a one-dimensional or two-dimensional matrix. The image detector can, in particular, comprise at least one camera. The at least one camera can, in particular, comprise a CCD camera. Alternatively, or in addition thereto, other kinds of image detectors can also be employed. The image detector can, in particular, comprise at least one CCD chip and/or at least one CMOS chip. Furthermore, the image detector can comprise at least one optical unit, for example at least one lens, which is configured to generate at least one image on a sensitive element of the image detector, for example on a sensor chip. In particular, the image detector can have at least one visual range, wherein the visual range, for example, comprises a solid angle and/or a distance in front of the image detector, within which the image data can be recorded. By way of example, the image detector can have at least one camera with fixed focus and/or adjustable focus and/or at least one autofocus camera. The image detector is configured to identify at least one property of the container.

Here, a property of the container is to be understood to mean a qualitatively and/or quantitatively recordable variable, which characterizes the container itself and/or substances contained in the container and/or a location of the container and/or an orientation of the container and/or contamination adhering to the container in a qualitative and/or quantitative manner. In order to identify the at least one property of the container, the image detector can, for example, have at least one image recognition. By way of example, the image detector can have at least one data processing device, which can be configured as a separate data processing device and/or which can also be wholly or partly integrated into a control of the cleaning and disinfecting apparatus. By way of example, this image recognition can comprise pattern recognition, wherein, in particular, commercial image recognition software can be employed. By way of example, the image detector can be configured to compare at least one recorded image of the container with a plurality of patterns and/or images stored in the data processing device and/or in a storage medium of the data processing device, as will still be explained in more detail below in an exemplary manner.

The data processing apparatus is furthermore configured to influence the cleaning program in accordance with the identified property. By way of example, the cleaning and disinfecting apparatus can, as explained above, comprise a centralized and/or decentralized control for this purpose, for example control with at least one data processing device which is configured in a program-technical manner. Here, in general, influencing the cleaning program is to be understood to mean a process in which at least one cleaning program parameter of the cleaning program is modified. By way of example, this can be one or more of the aforementioned cleaning program parameters. Examples of instances of influencing will still be explained in more detail below. Influencing can occur automatically, for example by virtue of the cleaning program automatically influencing one or more cleaning program parameters. Alternatively, or in addition thereto, the influencing can also occur with the involvement of a user or user of the cleaning and disinfecting apparatus, for example by virtue of at least one notification and/or at least one proposition and/or at least one warning being output to a user. This too can be considered to be influencing of the cleaning program since such an output of information to a user can, in principle, be a component of the cleaning program. Influencing the cleaning program can, in particular, comprise a composition of the cleaning program from one or more cleaning program steps or an embodiment of one or more cleaning program steps.

As explained above, the cleaning and disinfecting apparatus can, in particular, comprise one or more controls. This at least one control can, for example, comprise at least one data processing device, for example at least one microcomputer and/or microcontroller. Furthermore, the control can also, for example, comprise one or more interfaces for the purpose of interchanging information and/or commands with at least one operator and/or user and/or at least one further apparatus. By way of example, this at least one interface can comprise at least one display, on which information can be provided to a user and/or one or more acoustic and/or optical and/or haptic warning devices. Furthermore, the at least one interface can comprise at least one keyboard and/or another kind of human-machine interface. Furthermore, the interface can comprise at least one computer interface for connecting the cleaning and disinfecting apparatus to another computer and/or a data network.

In one embodiment of the cleaning and disinfecting apparatus, the at least one image detector can, in particular, be arranged outside of the cleaning chamber. By way of example, the image detector can be arranged on an external side of a sheath of the cleaning chamber, for example in a cover region and/or in a front region of the cleaning and disinfecting apparatus. The image detector can, in particular, be configured to identify the property prior to and/or during an insertion of the container into the cleaning chamber. By way of example, the image detector can be arranged on an external side of the cleaning chamber, wherein an input opening of the cleaning chamber, for example a door opening of a door to the cleaning chamber, is arranged in a visual range of the image detector, i.e., for example, within a solid angle range within which the image detector can record image data. By way of example, the input opening can have a movable door, in particular a flap. By way of example, the input opening can have a flap with a hinge, which is arranged in a front region and/or a cover region of the cleaning chamber. By way of example, the flap can pivot open toward the front, toward a user and/or operator. In particular, at least one holder for holding the container can be connected to the door. By way of example, this holder can be such that, when the door is open, the container is oriented in such a way that the content of the container remains in the container, for example by virtue of an opening of the container being oriented upward. While the door is being closed, the container can then, for example, be pivoted such that, for example, the content can flow out of the container during and/or after the act of closing. By way of example, the opening of the container can in the process be pivoted into a horizontal direction and/or into a downward-pointing direction.

As explained above, the image detector, in particular the camera, can preferably be arranged outside of the cleaning chamber. The image detector can be configured to record an image of the container prior to and/or during the insertion of the container into the cleaning chamber. Here, at least one image of the container prior to and/or during the insertion of the container into the cleaning chamber can be recorded and preferably stored. In general, an image is to be understood to mean a one-dimensional, two-dimensional or three-dimensional amount of optical information, with a two-dimensional image preferably being recorded.

An advantage of arranging the image detector outside of the cleaning chamber can, in particular, lie in an improvement of the quality of the image recording. Thus, an image detector arranged outside of the cleaning chamber, in particular a camera arranged outside of the cleaning chamber, can, in general, supply substantially better results than in the case of an arrangement within the cleaning chamber. By way of example, this can be due to the fact that, in general, the risk of soiling an optical unit of the image detector, in particular of soiling a lens, for example of a camera, can be significantly reduced by the arrangement outside of the cleaning chamber. Moreover, spillage of the content of the container can lead to falsified information in relation to the kind of loading of the container and hence, for example, to falsification of the property to be identified.

A further advantage of arranging the image detector outside of the cleaning chamber lies in the fact that it is already possible to undertake appropriate measures, which can emerge from the property recorded by the image detector, prior to the container being introduced into the cleaning chamber. Thus, for example, the operating staff can already undertake necessary corrections prior to, during or at the loading, for example without health risks or hygiene risks, in contrast to known arrangements. The risk of a malfunction can also be significantly reduced compared to the devices in which detection only occurs within the cleaning chamber. Thus, in principle, there is a significantly reduced risk of malfunctions occurring as a result of faulty, unsuitable or otherwise incorrectly introduced containers since, for example, error identification can already be carried out prior to closing a door of the cleaning chamber and/or directly at the start of closing a door of the cleaning chamber.

Within the scope of this disclosure, a holder should, in general, be understood to mean a device which is configured to hold the container and affix it relative to the holder. By way of example, this holder can comprise at least one rail, into which the container can be inserted. Alternatively, or in addition thereto, the holder can also comprise one or more brackets and/or one or more cavities, into which the container can be inserted and/or introduced. Here, the cleaning and disinfecting apparatus can have a fixed holder or else an interchangeable holder, for example by virtue of a kind of the holder being able to be adapted to the type of the container.

The image detector can, in particular, be configured to identify the property of the container in the holder when the door is open. By way of example, this can be brought about by virtue of the fact that the image detector is arranged outside of the cleaning chamber, for example on an external side of the cleaning chamber, wherein the image detector observes an input region, for example a pivot region of the door. In this manner, the at least one property can for example already be identified prior to introducing the container into the cleaning chamber, in particular prior to closing the door. This embodiment, as already explained above and as will be described in more detail below, in particular offers the advantage that incorrect loading and/or incorrect operations can at least in part already be identified prior to closing the container.

The cleaning and disinfecting apparatus, in particular the image detector, can, in particular, be configured to record at least one image of the at least one container to be introduced into the cleaning chamber prior to the door being closed and/or while the door is closed. In particular, at least one image of the container can be recorded directly prior to closing the door, for example within a period of time of 0-5 s prior to closing the door. The at least one image can, in particular, be stored in a data storage medium.

Alternatively, or in addition thereto, the cleaning and disinfecting apparatus, in particular the image detector, can, in particular, also be configured to record at least one image of the container after renewed opening of the door and/or during a renewed opening of the door, in particular after carrying out a cleaning program. In particular, it is possible, directly after the renewed opening of the door, to record at least one image of the now preferably cleaned container, for example within a period of time of 0-5 s after opening the door. The at least one image can in turn be stored, in particular, in a data storage medium.

If the cleaning and disinfecting apparatus is configured to record and store at least one image of the container, for example prior to and/or after carrying out the cleaning program, this image can optionally be stored with one or more additional items of information. By way of example, the at least one image can be stored with at least one timestamp and/or with at least one assignment to a cleaning program, for example a run cleaning program, to which the container is subjected or was subjected.

Alternatively, or in addition thereto, the at least one additional item of information can contain at least one item of information in respect of a user, for example a specific member of staff. This assignment can, for example, take place on the basis of an identification number. By way of example, the cleaning and disinfecting apparatus can be configured to record an electronic identifier of a user, for example by means of an RFID chip. The identification of the user can be stored as additional information or as part of the additional information together with the at least one image. By way of example, as a result of this it is possible to assign specific processes to a specific user. The operator of the cleaning and disinfecting apparatus therefore preferably generally has the option, on the basis of the at least one image, of monitoring a correct operation and possibly of identifying incorrect operations. Schooling measures can then be initiated if required.

The cleaning and disinfecting apparatus can, in particular, be configured to provide documentation of the cleaning process on the basis of the at least one image of the container recorded prior to and/or after running of the cleaning program, optionally using one or more additional items of information. If at least one image is recorded and stored, real-time image processing is, in particular, generally not required and can preferably be dispensed with. At the same time, an operator of the cleaning and disinfecting apparatus can prove on the basis of the images that the operating staff has operated the cleaning and disinfecting apparatus correctly and used suitable programs.

The cleaning and disinfecting apparatus, in particular the image detector, can, in particular, be configured to store and/or forward at least one image recorded by means of the image detector, for example at least one image of the container. By way of example, the cleaning and disinfecting apparatus, in particular the image detector, can be configured to forward the at least one image by at least one interface and/or by at least one data connection in a wireless and/or wired manner to at least one further device. Thus, the cleaning and disinfecting apparatus, in particular the image detector, can be configured to transmit and/or send the at least one image to the outside such that this image for example is available on a data processing device outside of the cleaning and disinfecting apparatus. By way of example, the at least one image can be stored and optionally processed in a computer, for example a PC, in a hygiene control room. Thus, the at least one image can optionally be stored, displayed and/or processed within the cleaning and disinfecting apparatus and/or in an external computer.

If at least one image is transmitted to an external data processing device, this external data processing device can then, for example, be configured to influence the at least one cleaning and disinfecting apparatus in accordance with a result of image processing, for example influence the at least one cleaning program. Within this meaning, the external data processing device can then notionally be part of the cleaning and disinfecting apparatus, for example as part of a control of the cleaning and disinfecting apparatus, even if this external data processing device for example is arranged outside of a housing of the cleaning and disinfecting apparatus which surrounds the cleaning chamber. Alternatively, or in addition thereto, the external data processing device can also form a cleaning and disinfecting system together with the cleaning and disinfecting apparatus.

In the external data processing device, for example in the external PC, it is then possible, for example, that the same routines run as described above or below in respect of the cleaning and disinfecting apparatus itself. By way of example, the cleaning and disinfecting apparatus and/or the external data processing device can be configured to carry out a comparison as to whether loading of the cleaning and disinfecting apparatus was admissible, as to whether the container was inserted correctly or similar evaluation operations.

In general, the cleaning and disinfecting apparatus can, in particular, be configured to output at least one warning to a user, for example a visual warning and/or an acoustic warning. By way of example, the warning can be output in accordance with a result of processing the at least one image. If processing of the at least one image, for example by the control and/or by an external data processing device, is very timely in relation to a program start of the cleaning program (for example, within the time span of no more than one minute, in particular of no more than 30 seconds) and if abnormalities are identified in the process, the control and/or the external data processing device can be configured to generate a response to the cleaning and disinfecting apparatus prior to and/or still during the program sequence. Thus, the cleaning and disinfecting apparatus can, for example, be configured to emit a warning at a program end to a user that the cleaning result should be examined in great detail.

The cleaning and disinfecting apparatus and/or an external data processing means can optionally be configured to communicate to a user and/or a responsible person one or more items of information in accordance with a result of processing the at least one image, for example electronically, in particular by email and/or SMS. Thus, the cleaning and disinfecting apparatus and/or an external data processing means can be configured to send, preferably immediately, an email to, e.g., a hygiene officer, either in the case of abnormalities or, collected, at selectable time intervals. The hygiene officer can then, for example, initiate appropriate schooling measures.

An advantage of using at least one external data processing device as part of a control of the cleaning and disinfecting apparatus and/or as an external device can, in particular, lie in a provision of resources. Thus, resources, e.g., computing capacity and/or memory, can be provided cost-effectively, even in the case of cramped spatial conditions in the cleaning and disinfecting apparatus. Moreover, common use can be made of resources of several cleaning and disinfecting apparatuses.

The control can, in particular, comprise at least one hygiene control component. The hygiene control component can, in particular, be a control component which is configured to assist a user in an evaluation of a cleaning effect and/or hygienization of the container by the cleaning program. Thus, the hygiene control component can, in particular, have one or more of the following functions: displaying at least one image of the container on a screen, documenting image data, storing image data, a database function, a forwarding function for image data, for example by email and/or MMS. The hygiene control component can, in particular, be wholly or partly implemented on at least one external data processing device, in particular on an external PC. In particular, the hygiene control component can be wholly or partly implemented as software component of the control. Thus, the hygiene control component can, for example, comprise a hygiene assistant in the form of a software component, for example a small computer program, which, in particular, can be wholly or partly installed on an external data processing device and/or on a central data processing device.

If provision is made for at least one hygiene control component, an operator of the cleaning and disinfecting apparatus can define a sampling mode, in particular in the hygiene control component, for example in the hygiene assistant. In particular, the hygiene control component can be configured to send queries for evaluating an operating sequence. By way of example, this can be brought about in the form of an email and/or an MMS with images to a responsible person, for example a hygiene officer. The responsible person can look at and evaluate the images and can make a decision as to whether the process sequence is objection-free or whether action is required as a result thereof. Image processing and/or image evaluation can then also be wholly or partly carried out by a human as an alternative or in addition to an image evaluation by the control. The result of the human assessment can, for example, in turn be communicated to the control, for example by means of buttons and/or a reply email to the hygiene assistant. Improved documentation of the work sequences can already emerge for the operator of the cleaning and disinfecting apparatus by this simple method.

The cleaning and disinfecting apparatus can furthermore have at least one illumination device. By way of example, this illumination device can be configured to illuminate a visual range of the image detector, at least in part. Accordingly, this illumination device can optionally be likewise arranged outside of the cleaning chamber, for example on an external side of the cleaning chamber. By way of example, the illumination device can comprise at least one incandescent lamp and/or at least one gas-discharge lamp and/or at least one semiconductor light source, for example at least one light-emitting diode. The illumination device can be configured to emit visible light. Alternatively, or in addition thereto, the illumination device can however also emit electromagnetic radiation in a different spectral range, for example in an infrared and/or ultraviolet spectral range. By way of example, this allows specific kinds of soiling adhering to the container and/or particular kinds of content of the container to be identified.

As described above, the cleaning and disinfecting apparatus can, in particular, have at least one holder for holding the container. In general, this holder can, for example, have at least one loading position outside of the cleaning chamber, wherein the goods to be cleaned can be introduced into the holder and/or removed from the holder in the loading position by a user. In the following text, the terms user and operator are used synonymously here, independently of whether or not, for example, this is schooled staff. The holder can furthermore have at least one cleaning position within the cleaning chamber, wherein the container is arranged in the cleaning position in the cleaning chamber and the cleaning fluid can be applied thereto.

The loading position can, in particular, be the above-described position when the door of the cleaning and disinfecting apparatus is open, wherein the holder for example is connected to the door. In general, the image detector can, in particular, be configured to identify the property of the loading position, for example when the door is open.

As explained above, the cleaning and disinfecting apparatus can, in particular, be configured to empty, in particular into an outflow, the container in the cleaning position and/or in a transition from the loading position into the cleaning position. As explained above, the holder can, in particular, be arranged in a door of the cleaning device, in particular in a front-side flap. The container can be pivoted, particularly during a transition from the loading position into the cleaning position, wherein the container is rotated about one or more virtual or real axes.

Further possible embodiments relate to the property that can be identified by means of the image detector. As described above, the at least one identifiable property can relate to the container itself and/or a content of the container and/or contamination adhering to the container and/or the location and/or position of the container in the holder. In particular, the property can be selected from the group consisting of: a kind of the container, in particular a container type and/or a container shape; a filling of the container with human excretions, in particular a filling amount and/or a kind of filling and preferably an identification as to whether or not a watery filling is present; a degree of soiling of the container; a kind of soiling of the container, for example soiling with balm residues, a suitability of the container for cleaning in the cleaning and disinfecting apparatus.

Here, within the scope of this disclosure, a degree of soiling can, in general, be understood to mean a grading of a soiling of at least one surface of the container, in which at least one of at least two categories of soiling is selected. By way of example, the degree of soiling can be specified by two, three or more categories, for example by virtue of using the categories "clean" and "soiled" or the categories "clean", "slightly soiled" and "strongly soiled" or a greater number of categories. In principle, a continuous description of the degree of soiling is also feasible, for example by virtue of an average reflectivity of the surface is recorded over a surface region of the container, wherein a reduction in the reflectivity for example allowing a greater degree of soiling to be deduced. Various other embodiments of assessing the degree of soiling are feasible. By way of example, the degree of soiling can be recorded optically, for example by means of a reflection measurement and/or an evaluation of a camera image, or in another manner.

Further possible embodiments relate to the kind of influencing of the cleaning program in accordance with the identified property. As explained above, at least one cleaning program parameter can, in particular, be influenced in the process. In particular, the influencing of the cleaning program can be selected from the group consisting of: a selection of a suitable cleaning program from a list of cleaning programs; a suggestion for a suitable cleaning program to a user of the cleaning and disinfecting apparatus; an influencing of at least one parameter of the cleaning program, in particular of a parameter selected from the group consisting of at least one cleaning program step in the cleaning program, a change in at least one concentration of at least one component of the cleaning fluid, in particular of a concentration of at least one cleaning agent and/or at least one disinfecting agent in the cleaning fluid and a temperature of the cleaning fluid; an actuation of various nozzles; an application on the goods to be cleaned by nozzles which change in position; an addition of at least one additional cleaning program step to the cleaning program; a prevention of the cleaning program and/or at least one subsequent cleaning program step of the cleaning program being carried out, for example if an unsuitable container and/or an unsuitable filling of the container and/or an incorrect location of the container is identified; an output of at least one warning and/or at least one notification to a user.

In particular, as described above, the cleaning and disinfecting apparatus can have at least one outflow. By way of example, the at least one outflow can be arranged in a base region of the cleaning chamber. By way of example, the cleaning chamber can, at least in part, taper in the form of a funnel and/or in a tilted manner toward the outflow in the base region. In particular, the outflow can have at least one odor trap, i.e., a device which is configured to keep gases from at least one outflow pipe connected to the outflow away from the interior of the cleaning chamber. By way of example, the odor trap can have at least one siphon bend. In particular, the cleaning and disinfecting apparatus can be configured to empty the container into the outflow during the cleaning program. As explained above, this emptying during the cleaning program can comprise automatic emptying and/or emptying which for example occurs during an introduction of the container into the cleaning chamber, for example while a door is closed, wherein, for example, a holder for the container is connected to the door and is pivoted while the door is being closed. Here, the closing of the door can be wholly or partly driven by a drive, for example by a motor, a mechanical system, a hydraulic system or a pneumatic system and/or can also be wholly or partly driven by muscle strength.

As known from, e.g., DE 103 48 344 A1, the cleaning and disinfecting apparatus can furthermore have at least one bypass, wherein gas and steam can be directed via the bypass into the outflow, preferably under pressure, from the cleaning chamber by circumventing the odor trap, for example by circumventing the siphon bend. By way of example, the bypass can comprise one or more pipes which connect the cleaning chamber with the outflow while circumventing the odor trap. By way of example, the bypass can furthermore have at least one check valve and/or at least one other kind of valve, which wholly or partly prevent the ingress of gases from the outflow and/or an outflow pipe connected to the outflow into the cleaning chamber through the bypass.

As described above, the fluid device can, in particular, comprise at least one liquid tank and at least one nozzle for applying a liquid to the container. Furthermore, the fluid device can, in particular, have at least one steam generator for generating hot steam and for applying hot steam to the container. In respect of possible embodiments, reference can once again be made to DE 103 48 344 A1 in an exemplary manner.

A further possible embodiment of the cleaning and disinfecting apparatus relates to the option of adapting the cleaning and disinfecting apparatus to specific kinds of containers and/or contents and/or contamination. In particular, the cleaning and disinfecting apparatus can be configured to carry out at least one learning program. By way of example, the at least one control of the cleaning and disinfecting device can be configured by program-technical means to enable this learning program. By way of example, at least one container with at least one known property can, in the learning program, be introduced into a visual range of the image detector by a user, in particular into a holder. The property can be identified by means of the image detector and the user can specify influencing of the cleaning program corresponding to the property and this can be stored in the cleaning and disinfecting apparatus. As a result of this, it is possible, by specification by the user, for one or more assignments to be created, in which one or more properties are in each case assigned one or more instances of influencing the cleaning program which are subsequently, after carrying out the learning program, usable during cleaning operation. By way of example, a user can in this manner specify specific cleaning programs in each case for the various container types and/or container kinds.

In particular, the cleaning and disinfecting apparatus, for example a control of the cleaning and disinfecting apparatus, can have at least one database. A plurality of identifiable properties and at least one instance of influencing of the cleaning program to be carried out for each property can be stored in the database. By way of example, this database can be complemented by repeatedly carrying out the above-described learning program. In general, the cleaning and disinfecting apparatus can, for example, be configured in such a way that carrying out the learning program is restricted to a specific user group. By way of example, the cleaning and disinfecting apparatus can have at least one authentication device, in particular, for example, an RFID reader. A different kind of authentication device is also feasible, for example an input field for entering a code, a card reader or similar kind of authentication device. The authentication device can, in general, be used to carry out an authentication of the user. In general, an authentication can be understood to mean an identification of a specific user and, optionally, a query as to whether the user is authorized to carry out one or more actions, for example, in general, to operate the cleaning and disinfecting apparatus and/or to carry out the learning program. By way of example, the cleaning and disinfecting apparatus can be configured in such a way that carrying out the learning program can be restricted to a specified user group.

In addition to the at least one image detector, the cleaning and disinfecting apparatus can comprise one or more further detectors, which can be configured to record one or more measurement variables. By way of example, the cleaning and disinfecting apparatus can have at least one process sensor in an interior of the cleaning chamber, in particular at least one optical process sensor. Here, in general, a process sensor is understood to mean a device which is configured to identify a degree of soiling of the container. The process sensor can, in particular, comprise at least one optical detector. Furthermore, the process sensor can comprise at least one illumination means. By way of example, the cleaning and disinfecting apparatus can be configured to modify a sequence of the cleaning program in accordance with the identified degree of soiling, in particular a composition of the cleaning program and/or at least one parameter of at least one cleaning program step of the cleaning program, for example a duration of the application of the cleaning fluid and/or a composition of the cleaning fluid. By way of example, the process sensor can be used at regular or irregular intervals to identify the degree of soiling of the container and a decision can be made, preferably automatically, on the basis of the degree of soiling and, for example, on the basis of possibly adhering soiling as to whether or not the cleaning program, for example an application of the cleaning fluid, should be continued. In respect of further possible embodiments of the process sensor, reference can, for example, be made to the aforementioned prior art, wherein the sensor systems known, for example, from dishwasher technology can also be used within the scope of the process sensor employed here. The process sensor particularly preferably comprises at least one further optical sensor, in particular at least one camera, which, for example once again by image identification and/or by reflection measurements on at least one surface of the container, can determine the degree of soiling.

The cleaning and disinfecting apparatus can furthermore be configured, for example by an appropriate program-technical means of the at least one control, to identify at least one cleaning result by means of the image detector after carrying out the cleaning program. By way of example, this can occur by means of the image detector optionally arranged on the external side of the cleaning and disinfecting apparatus, for example on an external side of the cleaning chamber of the cleaning and disinfecting apparatus, as soon as, for example, the door of the cleaning chamber is opened and/or as soon as the container is or has been brought into the loading position from the cleaning position. By way of example, this can occur when a flap of the cleaning and disinfecting apparatus is opened, for example when a flap is opened with a holder attached to this flap. Accordingly, the cleaning and disinfecting apparatus can, for example, be configured to output at least one item of information in respect of the cleaning result to a user, for example at least one item of information in respect of whether the cleaning result is correct or sufficient, or information in respect of the fact that there was insufficient cleaning, for example accompanied by a suggestion to carry out at least one further cleaning program and/or at least one further cleaning program step.

The cleaning and disinfecting apparatus can, in particular, have at least one warning device that emits at least one warning to a user. By way of example, this warning device can be a component of the above-described optional human-machine interface. By way of example, the warning device can be configured to output the warning by optical and/or acoustic and/or haptic and/or electronic means. By way of example, the warning device can comprise at least one display and/or at least one warning lamp. By way of example, the cleaning device can be configured to emit the warning if the identified property is selected from the group consisting of: the container is unsuitable for treatment in the cleaning and disinfecting apparatus; the container was not identified; the container is sealed; the container has been inserted incorrectly into a holder of the cleaning and disinfecting apparatus.

In a further aspect of this disclosure, a method for treating at least one container for human excretions is proposed. As explained above, this method can, in particular, be carried out using a cleaning and disinfecting apparatus in accordance with this disclosure. In respect of possible embodiments of the method, it is accordingly possible to refer to the preceding or subsequent description of preferred embodiments of the cleaning and disinfecting apparatus, or vice versa. At least one cleaning program is carried out in the method, for example a cleaning program in accordance with the description above with at least one cleaning program step. In the cleaning program, the container is emptied, in particular within a cleaning chamber. By way of example, this emptying, as described above, can occur when the cleaning chamber is being closed, for example by a user and/or automatically, and/or within the cleaning chamber and/or when transferring the container from a loading position into a cleaning position. By way of example, this emptying can occur by pivoting the container. At least one cleaning fluid is applied to the container in at least one cleaning chamber. By way of example, this can be brought about by at least one fluid device in accordance with the description above. At least one property of the container is identified by means of at least one image detector. Furthermore, the cleaning program is influenced in accordance with the identified property.

As explained above, the property can, in particular, be identified prior to and/or during an introduction of the container into the cleaning chamber, for example while closing at least one door of the cleaning chamber, wherein, preferably, at least one holder for the container is connected to the door.

The method can, in particular, be carried out in such a way that at least one image of the image detector is compared to a plurality of image patterns. In particular, use can be made of a plurality of image patterns stored in a control. By way of example, the cleaning program can be influenced in accordance with a result of the comparison. By way of example, it is possible, as described above, for at least one kind of influencing to be stored for each image pattern, wherein this kind of influencing is selected if the identified property corresponds to the respective stored image pattern.

As explained above, the method can, in particular, be carried out in such a way that at least one learning program is carried out. In the learning program, at least one container with at least one known property can be introduced into a visual range of the image detector by a user. This introduction of the container can, in particular, be brought about by means of a holder. The property can be identified by means of the image detector. The user can specify influencing of the cleaning program corresponding to the property, and this can be stored. By way of example, this specification can be brought about by virtue of the fact that a user selects an influencing of the cleaning program, for example by means of an appropriate keyboard and/or another kind of human-machine interface, which cleaning program should correspond to the identified property. In this manner, a user can, for example, specify specific properties and the respective influencing of the cleaning program in a targeted manner. By way of example, it is possible to specify specific kinds and/or types of containers, as well as corresponding cleaning programs. In turn alternatively, or in addition thereto, specific kinds of the filling and/or specific kinds of the soiling can be specified and corresponding cleaning programs for this can be specified and stored. In general, a database can be produced by repeatedly carrying out the learning program, wherein a plurality of identifiable properties and at least one instance of influencing of the cleaning program to be carried out for each property can be stored in the database.

As described above, the image detector is used to identify the at least one property of the container. However, the at least one image detector can additionally also be used to identify one or more further parameters. By way of example, the method and/or the cleaning and disinfecting apparatus can be configured in such a way that the image detector can be used to identify whether at least one object is situated in a danger area, for example in a danger area in front of an opening of the cleaning chamber. By way of example, the method and the cleaning device can be configured in such a way that the image detector is used to identify at least one object in at least one danger area of the cleaning and disinfecting apparatus, for example in a pivot region and/or movement region of a door of the cleaning and disinfecting apparatus. The cleaning and disinfecting apparatus can, in particular, be configured in such a way that when such an object is identified, a warning is output to a user, for example by means of the above-described warning device. By way of example, this renders it possible to identify that, when the door is opened, an object, for example a hand of a user, is arranged in a pivot region and/or movement region of the door, wherein, for example, a warning can occur and/or wherein a closing of the door and hence a squashing of the object can be prevented.

Compared to known methods and cleaning devices, the proposed method and the proposed cleaning device have a multiplicity of advantages. Thus, the image detector can, in particular, be realized in a simple manner with a camera, which can, for example, be configured to identify a load of the cleaning and disinfecting apparatus, by means of which the cleaning and disinfecting apparatus is loaded or is to be loaded. The image detector can create one or more images, i.e., for example, an individual image or sequence of images, which can be processed in a control of the cleaning and disinfecting apparatus, whereupon, accordingly, one or more reactions of the cleaning and disinfecting apparatus can be initiated.

The image detector can, in particular, be arranged outside of the cleaning chamber, for example outside of or in front of the cleaning chamber. The image detector can be securely connected to the cleaning chamber or else be arranged independently thereof as a separate detector. By way of example, the image detector can be arranged in a frame of the cleaning chamber or connected to a frame of the cleaning chamber. In particular, by arranging the image detector outside of an interior of the cleaning chamber, soiling of the image detector, for example an optical unit of the image detector, can be prevented in the best possible manner. Furthermore, this also allows a loading region of the cleaning chamber to be monitored. Moreover, better illumination conditions are usually found outside of the cleaning chamber, and so the image recognition can be supported by improved illumination.

The camera can have a simple design and can, for example, be embodied as autofocus camera or else as a fixed focus camera. It is optionally possible, as described above, to realize image recognition by illuminating a visual range, for example a recording region, so that identification also becomes possible in the case of, e.g., inexpedient surrounding light conditions.

Identifying the property of the container, for example the load, can in particular take place prior to and/or while closing a door of the cleaning chamber. Furthermore, an image comparison can, for example, be realized in a simple manner, for example with one or more image patterns in a catalog, which can, for example, be stored in a control.

The above-described option of realizing a learning program moreover offers a greatest possible flexibility of the proposed cleaning device and/or of the proposed method. In particular, one or more identifiable properties and corresponding reactions of the cleaning and disinfecting apparatus as an influence can be learned in this manner: a specific kind and/or shape of the container; a specific load of the container, for example a watery or non-watery load. Identified image patterns can be recorded in, e.g., a catalog, for example in a database.

The cleaning and disinfecting apparatus can be configured to identify admissible containers, such as, e.g., admissible vessels, collection bags or similar containers. If an unknown or inadmissible container is identified, information and/or, in particular, a warning can be output to a user and/or to another apparatus. The cleaning and disinfecting apparatus can be configured in such a way that the user must acknowledge the warning. The cleaning and disinfecting apparatus can furthermore be configured in such a way that the identification of an unknown or inadmissible container is logged, for example in a process log, wherein, for example, an acknowledgment of a warning by a user can also be logged, optionally including an identification of the user. The cleaning and disinfecting apparatus can, in general, be configured to create a log with sequence data of the cleaning program. By way of example, acknowledgment of the warning can be configured in such a way that the latter is made possible only with a personal identification, for example by a staff ID with chip, an RFID-ID or another kind of authentication device.

After identifying the introduced container, for example by a control, a program can be proposed by the cleaning and disinfecting apparatus, for example by optical highlighting of a corresponding program button, an acoustic announcement of a recommended program or a pre-selection by the control, which is activated, for example by closing the door.

Furthermore, operation errors when inserting the container can also be reliably identified. By way of example, it is possible to identify incorrectly inserted containers. This too can be summed under the property of the container, and so the at least one property of the container can, in general, also comprise a property of a positioning and/or orienting of the container in a holder. In this manner, it is, for example, also possible to identify that a container assumes an incorrect position, that a cover has not been removed or a similar property or combination of properties. In this case, it is once again possible to output a notification and/or a warning to a user, by means of which the incorrect operation can be highlighted.

In general, the proposed cleaning and disinfecting apparatus and the proposed method can increase hygiene safety. In particular, this is due to the fact that incorrect operations, which typically lead to reduced cleaning power and/or to a reduced disinfection result, can reliably be avoided. Furthermore, the operator of the cleaning and disinfecting apparatus can reliably identify incorrect operations, for example on the basis of a log. By way of example, reading the log and/or the history allows knowledge to be gained in relation to schooling requirements for the staff.

Advantages also emerge for the producer of the cleaning and disinfecting apparatus by the embodiment according to this disclosure. In addition to the above-described simple implementation, even in existing cleaning and disinfecting apparatuses, it is possible, for example, for the producer of the cleaning and disinfecting apparatus to observe a market, for example by virtue of evaluating collected logs. In this manner, it is also easier to implement corresponding legal requirements for medical products. In general, knowledge can be obtained in respect of product improvements, for example by virtue of evaluating user behavior.

Furthermore, the cleaning and disinfecting apparatus and the method can also be embodied in such a way that a cleaning result can be assessed at the program end after opening the door. This cleaning result can, for example, be indicated accordingly by an indication means, for example a display, or, for example, by means of a lamp. Thus, for example, use can be made of a simple red/green light, wherein, for example, a red light can light up for a cleaning result which is not in accordance with the specifications and a green light can light up for a cleaning result which is in accordance with the specifications. A cleaning program can accordingly be adapted, for example a cleaning program which follows the already complete cleaning of the same container or a cleaning program for another container. Thus, for example, it is possible, in accordance with the previously obtained cleaning results, to modify one or more cleaning program parameters of the subsequent cleaning program. Thus, for example, when dripping onto the containers, metering of one or more additives of the cleaning fluid can be modified and/or at least one drying step can be modified, for example, a time duration of at least one drying step can be increased. Other embodiments are also possible.

As explained above, the cleaning and disinfecting apparatus can be configured to store at least one process log, in which, for example, actual data of one or more sensors and/or of properties identified by means of the image detector can be logged, as well as optionally additional events. This process log can, for example, be stored in a data storage medium of the control of the cleaning and disinfecting apparatus and/or in the control itself. The cleaning and disinfecting apparatus and/or the control can, as explained above, also comprise at least one interface such that, for example, it is possible to transmit data of the process protocol to a further apparatus, for example a data teletransmission to a control room and/or into a service network of the producer. In this manner, the cleaning and disinfecting apparatus can also be reliably incorporated into a central apparatus control of, e.g., a hospital or a care home, wherein, from a control room and without personal presence in situ, it is also possible to monitor a cleaning result and/or correct operation and/or correct function of the cleaning and disinfecting apparatus. In this manner, there is increased process safety.

Furthermore, as described above, it is also possible, according to this disclosure, to secure a danger area. Thus, for example, it is possible to ensure that no moved and/or inadmissible objects are arranged in a danger area, for example in a pivot region of a door. If, for example, specific objects are identified in this danger area, for example an arm of a user, an inadmissible container or similar objects, it is possible, for example, for closing of the door to be prevented. Only after such objects are removed from the danger area can the process of closing the door be released. Overall, this allows the process safety to be significantly increased and risks of accidents can be avoided.

It is possible additionally to monitor the cleaning result by the above-described optional at least one process sensor, which is arranged in the interior of the cleaning chamber, for example an additional camera in the interior of the process chamber. By way of this process sensor it is possible, for example, to check and/or monitor a cleaning result while the cleaning program progresses. By way of example, a comparison with one or more specified images in a database can be carried out by means of a camera of the process sensor, for example once again by image detection, in order to monitor a cleaning result. In particular, the cleaning and disinfecting apparatus can be configured to monitor a cleaning result during the process of the cleaning program prior to a thermal disinfection. By way of example, as a result of this it is possible to prevent contamination from still adhering to the container as a result of an insufficient cleaning result and the thermal disinfection nevertheless being started; this could lead to solid baking of soiling residues. In accordance with the cleaning result identified by means of the process sensor, the cleaning and disinfecting apparatus can be configured to modify the cleaning program. By way of example, it is possible for one or more process parameters to be modified, in particular adapted, during the treatment. By way of example, the cleaning program and/or at least one cleaning program step of the cleaning program can optionally be lengthened. Alternatively, or in addition thereto, one or more washing processes can be complemented and/or an additional component can be metered into the cleaning fluid, for example an additional process chemical.

The cleaning and disinfecting apparatus can, in general, for example be realized as a front loader or else as a top loader. In the case of a front loader, a door, for example a swing door, is in this case arranged in the front region of the cleaning and disinfecting apparatus. In the case of a top loader, this door is arranged on a top side of the cleaning and disinfecting apparatus.

The at least one image detector can, for example, be fixedly connected to a housing of the cleaning chamber. Alternatively, or in addition thereto, the at least one image detector can also be arranged next to the housing as a separate component, wherein nevertheless a connection can be established to, for example, a control of the cleaning and disinfecting apparatus. This connection can, for example, have a wired or wireless design. In general, the image detector can be configured in such a way that containers have to pass at least once through a visual range of the image detector prior to them being introduced into the cleaning chamber. By way of example, this can occur prior to, during or after an introduction of the at least one container into a holder.

In summary, the following features within the scope of this disclosure:

Embodiment 1

A cleaning and disinfecting apparatus for treating at least one container for human excretions, comprising at least one cleaning chamber with at least one fluid device for applying at least one cleaning fluid to the container, wherein the cleaning and disinfecting apparatus is configured to carry out at least one cleaning program, wherein, in the cleaning program, the container is emptied and the cleaning fluid is applied thereto, wherein the cleaning and disinfecting apparatus furthermore has at least one image detector, wherein the image detector is configured to identify at least one property of the container and wherein the cleaning and disinfecting apparatus is configured to influence the cleaning program in accordance with the identified property.

Embodiment 2

The cleaning and disinfecting apparatus as described in the preceding embodiment, wherein the image detector is arranged outside of the cleaning chamber.

Embodiment 3

The cleaning and disinfecting apparatus as described in the preceding embodiment, wherein the cleaning and disinfecting apparatus, in particular the image detector, is configured to identify the property prior to and/or during an insertion of the container into the cleaning chamber.

Embodiment 4

The cleaning and disinfecting apparatus as described in one of the two preceding embodiments, wherein the cleaning and disinfecting apparatus, in particular the image detector, is configured to identify the property after completion of a cleaning program.

Embodiment 5

The cleaning and disinfecting apparatus as described in one of the three preceding embodiments, wherein the image detector is arranged on an external side of the cleaning chamber and wherein an input opening of the cleaning chamber is arranged at least in part in a visual range of the image detector.

Embodiment 6

The cleaning and disinfecting apparatus as described in one of the preceding embodiments, wherein the cleaning and disinfecting apparatus has a movable door, more particularly a flap, wherein at least one holder for holding the container is connected to the door, wherein the image detector is configured to identify the property of the container in the holder when the door is open.

Embodiment 7

The cleaning and disinfecting apparatus as described in one of the preceding embodiments, wherein the cleaning and disinfecting apparatus is configured to capture and preferably store at least one image of the container.

Embodiment 8

The cleaning and disinfecting apparatus as described in the preceding embodiment, wherein the cleaning and disinfecting apparatus is configured to store at least one additional item of information together with the image.

Embodiment 9

The cleaning and disinfecting apparatus as described in the preceding embodiment, wherein the additional item of information is selected from the group consisting of: information relating to a user of the cleaning and disinfecting apparatus; information relating to a time of recording of the image, in particular a timestamp.

Embodiment 10

The cleaning and disinfecting apparatus as described in one of the preceding embodiments, wherein the cleaning and disinfecting apparatus furthermore has at least one illumination device, wherein the illumination device is configured to at least partly illuminate a visual range of the image detector.

Embodiment 11

The cleaning and disinfecting apparatus as described in one of the preceding embodiments, wherein the cleaning and disinfecting apparatus has at least one holder for holding the container, wherein the holder has at least one loading position outside of the cleaning chamber, wherein, in the loading position, the container can be introduced into the holder and removed from the holder by a user, wherein the holder furthermore has at least one cleaning position within the cleaning chamber, wherein the container is arranged in the cleaning chamber in the cleaning position and the cleaning fluid can be applied thereto.

Embodiment 12

The cleaning and disinfecting apparatus as described in the preceding embodiment, wherein the image detector is configured to identify the property in the loading position.

Embodiment 13

The cleaning and disinfecting apparatus as described in one of the two preceding embodiments, wherein the cleaning and disinfecting apparatus is configured to empty, in particular into an outflow, the container in the cleaning position and/or during a transition from the loading position into the cleaning position.

Embodiment 14

The cleaning and disinfecting apparatus as described in one of the three preceding embodiments, wherein the holder is at least partly arranged in a door of the cleaning device, in particular in a front-side flap.

Embodiment 15

The cleaning and disinfecting apparatus as described in one of the four preceding embodiments, wherein the container is pivoted during a transition from the loading position into the cleaning position.

Embodiment 16

The cleaning and disinfecting apparatus as described in one of the preceding embodiments, wherein the image detector comprises at least one camera and at least one image recognition device.

Embodiment 17

The cleaning and disinfecting apparatus as described in one of the preceding embodiments, wherein the property is selected from the group consisting of: a kind of the container, in particular a container type and/or a container shape; a filling of the container with human excretions, in particular a filling amount and/or a kind of filling and preferably an identification as to whether or not a watery filling is present; a degree of soiling of the container; a kind of soiling of the container; a suitability of the container for cleaning in the cleaning and disinfecting apparatus; a location and/or position of the container.

Embodiment 18

The cleaning and disinfecting apparatus as described in one of the preceding embodiments, wherein the influencing of the cleaning program is selected from: a selection of a suitable cleaning program from a list of cleaning programs; a suggestion for a suitable cleaning program to a user of the cleaning and disinfecting apparatus; an influencing of at least one parameter of the cleaning program, in particular of a parameter selected from the group consisting of a duration of at least one cleaning program step in the cleaning program, a change in at least one concentration of at least one component of the cleaning fluid, in particular of a concentration of at least one cleaning agent and/or at least one disinfecting agent in the cleaning fluid; a temperature of the cleaning fluid and/or a different actuation of various nozzles; an application on the goods to be cleaned by nozzles which change in position, in particular at least one lift/rotation nozzle; a prevention of the cleaning program and/or at least one subsequent cleaning program step of the cleaning program being carried out; an addition of at least one additional cleaning program step to the cleaning program; an output of at least one warning and/or at least one notification to a user.

Embodiment 19

The cleaning and disinfecting apparatus as described in one of the preceding embodiments, wherein the cleaning and disinfecting apparatus has at least one outflow with at least one odor trap, wherein the cleaning and disinfecting apparatus is configured to empty the container into the outflow during the cleaning program.

Embodiment 20

The cleaning and disinfecting apparatus as described in the preceding embodiment, wherein the cleaning and disinfecting apparatus furthermore has at least one bypass, wherein gas and steam can be directed into the outflow, preferably under pressure, from the cleaning chamber through the bypass by circumventing the odor trap.

Embodiment 21

The cleaning and disinfecting apparatus as described in one of the preceding embodiments, wherein the fluid device comprises at least one liquid tank and at least one nozzle for applying a liquid to the container, wherein the fluid device furthermore has at least one steam generator for generating hot steam and for applying the steam to the container.

Embodiment 22

The cleaning and disinfecting apparatus as described in one of the preceding embodiments, wherein the cleaning and disinfecting apparatus is furthermore configured to carry out at least one learning program, wherein, in the learning program, at least one container with at least one known property is introduced into a visual range of the image detector by a user, in particular in a holder, wherein the property is identified by means of the image detector and an influencing of the cleaning program corresponding to the property can be specified by the user and can be stored in the cleaning and disinfecting apparatus.

Embodiment 23

The cleaning and disinfecting apparatus as described in the preceding embodiment, wherein the cleaning and disinfecting apparatus, in particular a control of the cleaning and disinfecting apparatus, has at least one database, wherein a plurality of identifiable properties and, for each property, respectively at least one influencing of the cleaning program to be carried out are stored in the database.

Embodiment 24

The cleaning and disinfecting apparatus as described in one of the two preceding embodiments, wherein the cleaning and disinfecting apparatus has at least one authentication device, in particular an RFID reader, wherein the authentication device can be used to carry out an authentication of the user and wherein carrying out the learning program can be restricted to a specified user group.

Embodiment 25

The cleaning and disinfecting apparatus as described in one of the preceding embodiments, wherein the cleaning and disinfecting apparatus furthermore has at least one process sensor, more particularly an optical process sensor, in an interior space of the cleaning chamber, wherein the process sensor is configured to identify a degree of soiling of the container, wherein the cleaning and disinfecting apparatus is configured to modify a sequence of the cleaning program, in particular a composition of the cleaning program and/or at least one parameter of at least one cleaning program step of the cleaning program, in accordance with the identified degree of soiling.

Embodiment 26

The cleaning and disinfecting apparatus as described in one of the preceding embodiments, wherein the cleaning and disinfecting apparatus is furthermore configured to identify at least one cleaning result by means of the image detector after carrying out the cleaning program.

Embodiment 27

The cleaning and disinfecting apparatus as described in one of the preceding embodiments, wherein the cleaning and disinfecting apparatus is configured in such a way that at least one object in at least one danger area of the cleaning and disinfecting apparatus is identified by means of the image detector.

Embodiment 28

The cleaning and disinfecting apparatus as described in one of the preceding embodiments, wherein the cleaning and disinfecting apparatus has at least one warning device for outputting at least one warning to a user.

Embodiment 29

The cleaning and disinfecting apparatus as described in the preceding embodiment, wherein the cleaning device is configured to output the warning when the identified property is selected from the group consisting of: the container is unsuitable; the container was not identified; the container is sealed; the container has been inserted incorrectly into a holder; at least one inadmissible object is situated in a danger area of the cleaning and disinfecting apparatus.

Embodiment 30

A method for treating at least one container for human excretions, in particular by using a cleaning and disinfecting apparatus as claimed in one of the preceding claims, wherein at least one cleaning program is carried out, wherein the container is emptied in the cleaning program, in particular within a cleaning chamber, wherein at least one cleaning fluid is applied to the container in at least one cleaning chamber, wherein at least one property of the container is identified by means of at least one image detector and wherein the cleaning program is influenced in accordance with the identified property.

Embodiment 31

The method as described in the preceding embodiment, wherein the property is identified prior to and/or during an introduction of the container into the cleaning chamber.

Embodiment 32

The method as described in one of the two preceding embodiments, wherein at least one image of the image detector is compared to a plurality of image patterns, in particular to a plurality of image patterns stored in a control, wherein the cleaning program is influenced in accordance with a result of the comparison.

Embodiment 33

The method as claimed in one of the preceding embodiments relating to a method, wherein, furthermore, at least one learning program is carried out, wherein, in the learning program, at least one container with at least one known property is introduced into a visual range of the image detector by a user, in particular in a holder, wherein the property is identified by means of the image detector and wherein an influencing of the cleaning program corresponding to the property is specified and stored by the user.

Embodiment 34

The method as described in the preceding embodiment, wherein a database is created by repeatedly carrying out the learning program, wherein a plurality of identifiable properties and, for each property, respectively at least one influencing of the cleaning program to be carried out are stored in the database.

Embodiment 35

The method as described in one of the preceding embodiments relating to a method, wherein at least one image of the container is recorded by means of the image detector.

Embodiment 36

The method as described in the preceding embodiment, wherein the at least one image is forwarded to at least one external data processing device.

Embodiment 37

The method as described in the preceding embodiment, wherein the external data processing device subjects the at least one image to image processing.

BRIEF DESCRIPTION OF THE DRAWINGS

Further details and features of this disclosure emerge from the following description of exemplary embodiments. The invention is not restricted to the exemplary embodiments. The exemplary embodiments are depicted schematically in the figures. Here, the same reference signs in the individual figures denote the same or functionally equivalent elements, or elements corresponding to one another in terms of their functions.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
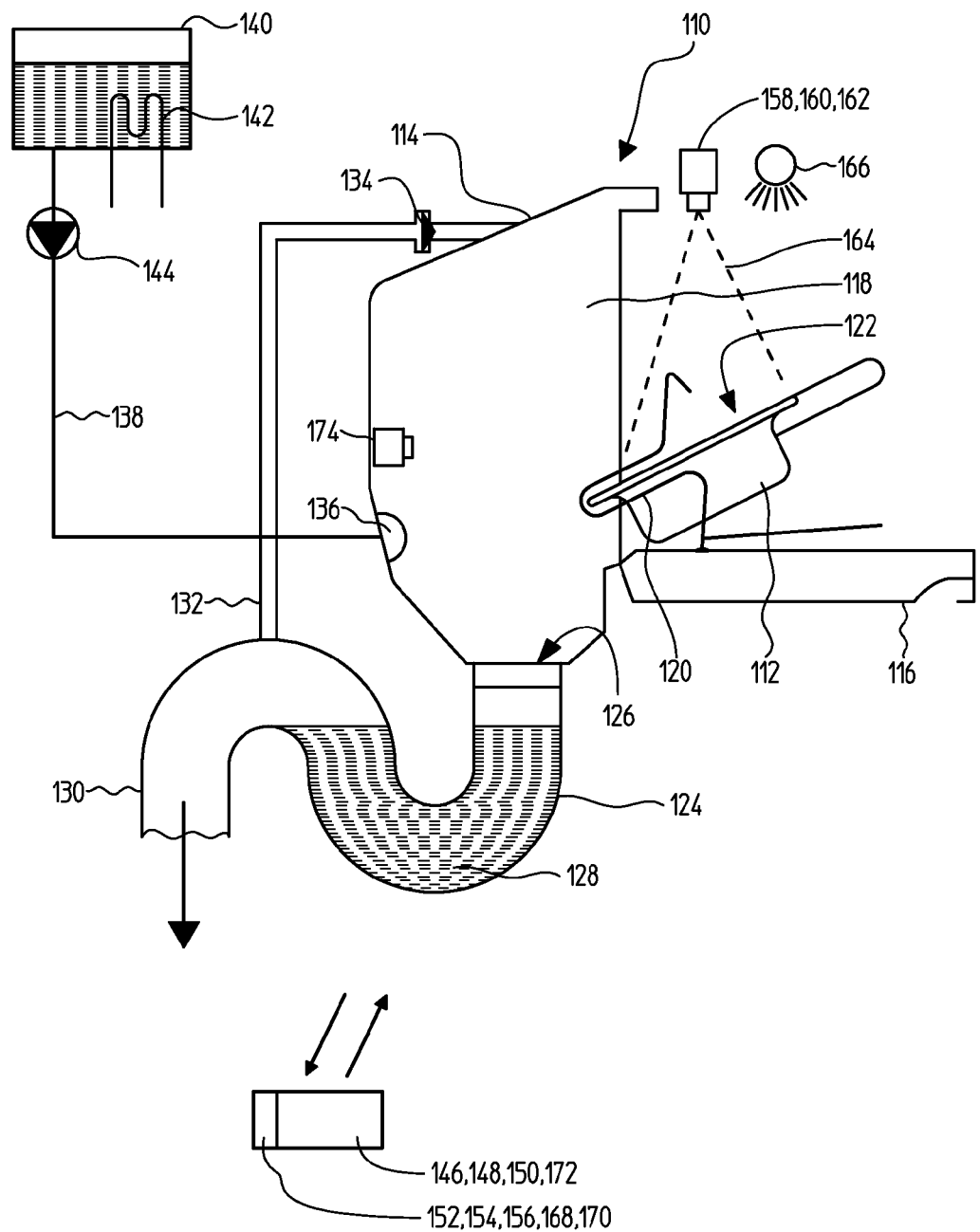
FIG. 1 shows a cleaning and disinfecting apparatus according to this disclosure, with a holder in a loading position.
Figure 2:
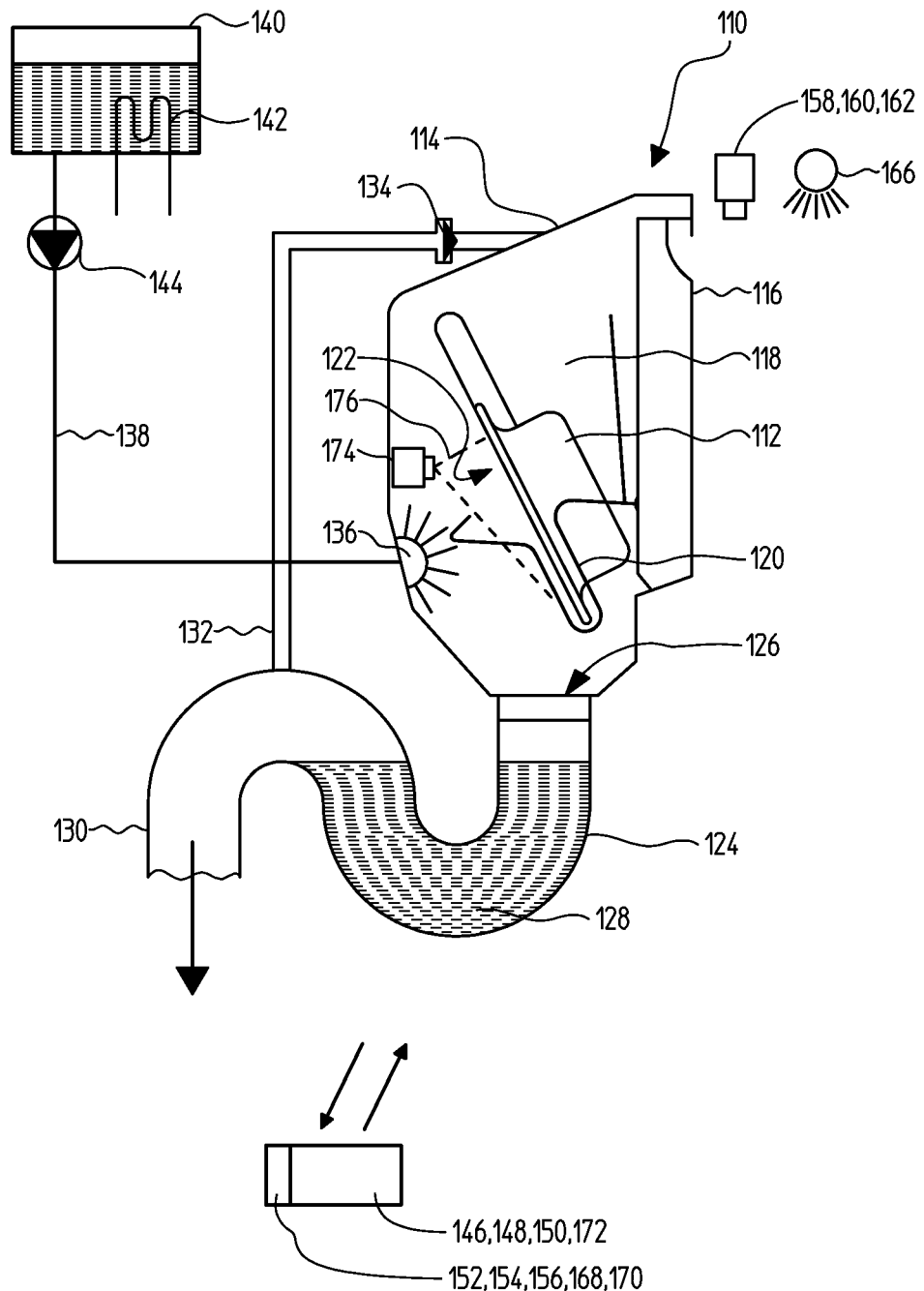
FIG. 2 shows the cleaning and disinfecting apparatus in accordance with FIG. 1, with the holder in a cleaning position.

In the following, an exemplary embodiment of a cleaning and disinfecting apparatus 110, for treating at least one container 112 for human excretions, is shown in different positions. Here, FIG. 1 depicts a schematic sectional illustration of the cleaning and disinfecting apparatus 110 in a loading position, which is described in more detail below, whereas FIG. 2 shows the exemplary embodiment in accordance with FIG. 1 in a cleaning position. In the following, both figures are explained together.

The cleaning and disinfecting apparatus 110 comprises a cleaning chamber 114 with a door 116, by means of which an interior 118 of the cleaning chamber 114 is accessible. In the depicted exemplary embodiment, the door 116 is configured as a front flap, and so the cleaning and disinfecting apparatus 110, in general, is designed as a front loader. However, other embodiments are, in principle, also possible. The door 116 can be opened and/or closed automatically, for example by means of at least one drive (not depicted in the figures) or else, alternatively, or in addition thereto, by manual operation by a user.

A holder 120 is arranged on a side of the door 116 facing the interior 118. By way of example, this holder 120 can comprise wire rods and/or a wire basket and/or another kind of holder 120. In FIG. 1, the door 116 is depicted in an opened state and the holder 120 is situated in a loading position. In this loading position, the container 112, a bedpan in the depicted exemplary embodiment, can be inserted into the holder 120 in such a way that a content of the container 112 cannot flow out. By way of example, this can be brought about by virtue of the fact that an opening 122 of the container 112 points upward or upward at an angle. By contrast, in FIG. 2, the door 116 is depicted in a closed position and the holder 120 is situated in a cleaning position. In this cleaning position, the opening 122 of the container 112 preferably points downward or at least downward at an angle such that the content of the container 112 can flow out into the interior 118 of the cleaning chamber 114 while and/or after closing the door 116. On the base of the cleaning chamber 114, provision is made for an outflow 124 with an outflow opening 126, having appropriately large dimensions, for example with a diameter or equivalent diameter of greater than 30 mm, preferably of at least 50 mm or even at least 70 mm, or even 100 mm or more, through which outflow opening relatively large amounts of waste can be disposed of. The outflow 124 is preferably provided with an odor trap 128, for example a siphon bend, and is preferably connected to one or more outflow pipes 130. Provision can optionally be made for at least one bypass 132, which connects the interior 118 of the cleaning chamber 114 to the outflow 124 and/or the outflow pipe 130 while circumventing the odor trap 128. In this bypass 132, provision can be made for at least one valve 134, for example a nonreturn valve and/or check valve. By means of the bypass 132, steam and/or gases can, for example, be displaced out of the interior 118 by force and into the outflow 124, for example by means of at least one pressure nozzle (not depicted in the figures) to the cleaning chamber 114, by means of which, e.g., air can be pressed into the cleaning chamber 114 in order to cool the container 112 and/or in order to displace steam into the outflow 124.

At least one fluid device 136 is provided in the cleaning chamber 114. By way of example, this fluid device 136 can comprise one or more nozzles, into which at least one cleaning fluid can be applied by means of at least one supply line 138. By way of example, the supply line 138 can be fed from one or more fluid tanks 140. The at least one fluid tank 140 can optionally have at least one heating device 142 in order to wholly or partly warm the cleaning fluid. In order to supply the cleaning fluid to the at least one nozzle under pressure, at least one pump 144 can furthermore be provided in the fluid tank 140 and/or in the supply line 138. The fluid device 136 and/or the cleaning and disinfecting apparatus 110 can furthermore have at least one steam generator, which is not depicted in FIGS. 1 and 2 and by means of which, for example after a fluid has been applied, there can be a disinfection of the container 118 with hot steam, for example by the supply line 138 and/or a separate supply line.

The cleaning and disinfecting apparatus 110 furthermore has at least one control 146, which is merely depicted schematically in the figures. By way of example, this control 146 can comprise at least one data processing device 148 with optionally at least one data storage medium 150. The control 146 is configured to carry out at least one cleaning program of the cleaning and disinfecting apparatus 110. By way of example, the cleaning program can be started automatically or else by an action of a user, for example by closing the door 116 and/or actuating a button and/or actuating a switch, for example a foot switch. Accordingly, the control 146 can, for example, act on one, some or all of the aforementioned elements and can be configured to set current values of one or more cleaning program parameters. By way of example, the pump 144 and/or the heating device 142 and/or a mechanism for closing the door 116 and/or one or more valves and/or an operation of the steam generator can be controlled by the control 146. In this manner it is possible, for example, to carry out a cleaning program which, after an insertion of the container 112 into the holder 120 by a user, provides for closing the door 116 and, in the process, emptying the container 112. During the emptying, a content of the container 112 can, for example, be wholly or partly disposed of into the outflow 124. The cleaning program can subsequently comprise one or more washing steps, during which cleaning fluid is applied to the container 112 on one side or on several sides, for example by virtue of an interior of the container 112 being sprayed on. It is optionally subsequently possible for one or more disinfection steps to be carried out, during which there can be chemical and/or thermal disinfection. By way of example, there can be chemical disinfection by spraying and/or sprinkling a cleaning fluid with at least one disinfection agent additive. By way of example, as explained above, thermal disinfection can occur using at least one steam generator, in which hot steam is applied to the container 112. It is subsequently possible to carry out one or more drying steps. During the drying steps, it is also possible, for example, to blow or press supply air into the cleaning chamber 114, wherein, for example, hot steam or humidity can be displaced from the cleaning chamber 114 into the outflow 124 through the bypass 132. The door 116 can subsequently be opened or a door opening can be released. The control 146 can comprise one or more interfaces 152, for example one or more human-machine interfaces and/or one or more interfaces 152 for connecting the cleaning and disinfecting apparatus 110 to one or more further apparatuses and/or one or more data networks. In particular, the interface can comprise at least one indication device 154, for example one or more indication displays and/or one or more optical and/or acoustic indication elements such as, for example, one or more optionally colored lamps. By way of example, provision can be made for a green lamp and a red lamp. An acoustic output can also be provided. Furthermore, provision can be made for a human-machine interface in the form of at least one operating element 156, for example in the form of at least one keyboard and/or at least one button or switch. The indication device 154 and the operating element 156 can also be wholly or partly combined, for example in the form of a touchscreen.

The cleaning and disinfecting apparatus 110 furthermore comprises at least one image detector 158. In particular, as explained above, the at least one image detector 158 can comprise at least one camera 160. The image detector 158 can furthermore comprise at least one image recognition device 162. In FIGS. 1 and 2, this image recognition device 162 is plotted symbolically at the location of the camera 160. However, alternatively, or in addition thereto, the image recognition device 162 can also wholly or partly be a component of the control 146, for example by virtue of the data processing device 148 being configured by program-technical means for carrying out at least one image identification program. By way of example, the camera 160 can be connected directly or indirectly to the control 146. However, alternatively, or in addition thereto, the image recognition device 162 can also be wholly or partly arranged at the location of the camera 160, for example in the form of a microcontroller, and/or can be wholly or partly integrated into the camera 160. The image detector 158, in particular the camera 160, is preferably arranged wholly or partly outside of the interior 118 of the cleaning chamber 114, for example on an external side of the housing of the cleaning chamber 114, in the depicted exemplary embodiment. Here, the camera 160 can, for example, be directly or indirectly connected to the cleaning chamber 114, or else it can be arranged separate therefrom.

The image detector 158 is preferably arranged in such a way that, during or after the introduction of the container 112 into the holder 120, the container 112 passes at least once through a visual range 164 of the image detector 158. The image detector 158 can be embodied and/or aligned in such a way that the container 112, when the latter is inserted into the holder 120 in the loading position depicted in FIG. 1, is arranged in the visual range 164, preferably in such a way that the opening 122 of the container 112 lies in the visual range 164. In particular, this allows a filling and/or contamination of the container 112 to be identified. In general, the cleaning and disinfecting apparatus is configured to identify at least one property of the container 112, for example a kind and/or a type of the container 112 and/or a filling of the container 112 and/or a positioning of the container 112 and/or a contamination of the container 112, by means of the image detector 158. Additionally, the cleaning and disinfecting apparatus 110 can also be configured to detect inadmissible objects, for example an arm of a user, in the visual range 164 by means of the image detector 158. In order to support the image recognition and/or for supporting recognition of the at least one property, the image detector 158, as depicted in FIGS. 1 and 2, can furthermore have at least one illumination device 166, for example an illumination device which is configured to wholly or partly illuminate the visual range 164 of the image detector 158 and thereby, for example, improve a contrast and/or a brightness of an image captured by means of the image detector 158.

The cleaning and disinfecting apparatus 110 can influence at least one cleaning program in accordance with the at least one identified property. By way of example, the cleaning program can thus be adapted to the kind and/or the type of the container 112 and/or to a kind and/or amount of a filling of the container 112 and/or to a kind and/or amount of contamination of the container 112. By way of example, it is possible for program durations of one or more of the aforementioned washing steps to be adapted to the degree of contamination. In accordance with the kind of contamination, it is also possible to select one or more additives for the cleaning fluid in a targeted manner, for example an additive of at least one balm cleaner in order to remove balm residues. Furthermore, it is also possible, for example, to select a number and/or a selection of nozzles of the fluid device 136 and/or an alignment of one or more nozzles in accordance with the identified type of the container 112. Furthermore, it is possible for inadmissible containers 112 to be identified and for appropriate warnings to be output to a user, for example by means of the indication device 154 and/or a warning device 168, for example if a kind and/or a type of the container 112 is not identified or is identified as being inadmissible. The control 146, in particular the interface 152, can, in particular, comprise at least one authentication device 170, for example an input field for entering a user code and/or a card reader for reading a user ID and/or an RFID reader for reading a user chip such that a user of the cleaning and disinfecting apparatus 110 can be identified. Accordingly, it is possible, for example, to log when a user acknowledges a warning. In general, the control 146 can, for example, be configured to create a log of the cleaning of the container 112 and, for example, to store it in the data storage medium 150.

By way of example, at least one database, in which, for example, one or more instances of influencing of the cleaning program are respectively associated with one or more identified properties of the container 112, that is to say, for example, in each case one or more data records to be used with in each case one or more cleaning program parameters, can furthermore also be contained in the data storage medium 150. In accordance with the identified property, the cleaning and disinfecting apparatus 110 can, for example, automatically undertake the influencing or can undertake an influencing to the extent that at least one instance of influencing, for example at least one specific cleaning program, is suggested to a user, for example by means of the indication device 154, wherein the user can, for example, also make a selection from several proposed cleaning programs. By way of example, this selection can be made by means of one or more operating elements 156 and can, for example, also be logged in turn.

Furthermore, the cleaning and disinfecting apparatus 110, for example the control 146, can also be configured to carry out at least one learning program. This learning program too can be initiated in turn by means of, e.g., the authentication device 170 such that, for example, the learning program can only be carried out by a specific user group. In this manner, a user can, e.g., successively introduce several different containers 112 and/or differently filled containers 112 and/or containers 112 soiled to a different degree into the holder 120 and/or into the visual range 164 in another manner and can correspondingly specify an influencing of the cleaning program. By way of example, it is thus possible for a user to specify a specific cleaning program for a specific kind of the filling and/or for a specific kind of soiling and/or for a specific type of the container 112. By way of example, this cleaning program can be stored in a database 172 in the data storage medium 150. During subsequent operation, there can, for example, be automatic selection of influencing in accordance with this database.

The cleaning and disinfecting apparatus 110 can furthermore be configured to record and optionally evaluate a cleaning result after carrying out the cleaning program, optionally after opening the door 116, for example once again by means of the image detector 158, for example once again in the loading positions shown in FIG. 1. Accordingly, the cleaning result can, for example, be logged and/or brought to the user's attention by the indication device 154 and/or an appropriate warning can be output by means of the warning device 168. There can also be automatic influencing of one or more cleaning program parameters of subsequent cleaning programs.

Furthermore, as likewise depicted as an option in FIGS. 1 and 2, the cleaning and disinfecting apparatus 110 can comprise one or more process sensors 174, which can, for example, be arranged in the interior 118 of the cleaning and disinfecting apparatus 110. By way of example, this at least one process sensor 174 can in turn comprise at least one camera and/or another kind of sensor, for example an optical sensor. In principle, other sensors are also possible. By way of example, provision can be made for at least one optical sensor, which can carry out at least one reflection measurement on at least one surface of the container 112. In this manner, adhering contamination on this surface can be detected. By way of example, the process sensor 174 can be embodied in such a way that the latter has a visual range (reference sign 176 in FIG. 2) which at least partly covers the opening 122 of the container 112 in the cleaning position shown in FIG. 2 such that, for example, at least one internal surface of the container 112 can be recorded by means of the process sensor 174 and such that a cleaning result can, for example, be detected there. Like the image detector 158, the process sensor 174 can, for example, also be connected to the control 176.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

| LIST OF REFERENCE SIGNS | |
|---|---|
| 110 | Cleaning and disinfecting apparatus |
| 112 | Container |
| 114 | Cleaning chamber |
| 116 | Door |
| 118 | Interior |
| 120 | Holder |
| 122 | Opening |
| 124 | Outflow |
| 126 | Outflow opening |
| 128 | Odor trap |
| 130 | Outflow pipe |
| 132 | Bypass |
| 134 | Valve |
| 136 | Fluid device |
| 138 | Supply line |
| 140 | Fluid tank |
| 142 | Heating device |
| 144 | Pump |
| 146 | Control |
| 148 | Data processing device |
| 150 | Data storage medium |
| 152 | Interface |
| 154 | Indication device |
| 156 | Operating element |
| 158 | Image detector |
| 160 | Camera |
| 162 | Image recognition device |
| 164 | Visual range |
| 166 | Illumination device |
| 168 | Warning device |
| 170 | Authentication device |
| 172 | Database |
| 174 | Process sensor |
| 176 | Visual range of the process sensor |

What is claimed is:

1. A cleaning and disinfecting apparatus for treating a container for human excretions, comprising:
  a cleaning chamber having a fluid device for applying a cleaning fluid to the container;
  a holder for holding the container, the holder having a loading position outside of the cleaning chamber and a cleaning position within the cleaning chamber, wherein, in the loading position the container can be introduced into the holder and removed from the holder by a user, and in the cleaning position the cleaning fluid can be applied to the container positioned in the holder;
  an outflow comprising an odor trap;
  the apparatus configured to carry out a cleaning program comprising the following steps:
    emptying the container automatically, wherein, when emptying, the container is pivoted and/or tilted from a transport position in which the container contents remain in the container into an emptying position in which the container points downward such that the container contents can flow out of the container and into the outflow;
    applying the cleaning fluid to the container; and
  an image detector arranged outside of the cleaning chamber and being configured to identify a property of the container prior to and/or during insertion of the container into the cleaning chamber, wherein the processor is configured to influence the cleaning program in accordance with the identified property;
  wherein the identified property is selected from the group consisting of: a kind of the container, a filling of the container with human excretions, a degree of soiling of the container, a kind of soiling of the container, a suitability of the container for cleaning in the cleaning and disinfecting apparatus, one or both of a location or a position of the container.

2. The cleaning and disinfecting apparatus as claimed in claim 1, wherein the image detector comprises at least one camera.

3. The cleaning and disinfecting apparatus as claimed in claim 1, further comprising a movable door, at least one holder for holding the container being connected to the door, wherein the image detector is configured to identify the property of the container in the holder when the door is open.

4. The cleaning and disinfecting apparatus as claimed in claim 3, wherein the movable door is a flap.

5. The cleaning and disinfecting apparatus as claimed in claim 1, wherein the image detector is configured to identify the property in the loading position.

6. The cleaning and disinfecting apparatus as claimed in claim 1, wherein the property is a kind of the container, wherein the kind of the container is one or both of a container type or a container shape.

7. The cleaning and disinfecting apparatus as claimed in claim 1, wherein the property is a filling of the container with human excretions, wherein the filling of the container is one or both of a filling amount or a kind of filling.

8. The cleaning and disinfecting apparatus as claimed in claim 1, wherein the property is a filling of the container with human excretions, wherein the filling of the container is an identification as to whether or not a watery filling is present.

9. The cleaning and disinfecting apparatus as claimed in claim 1, wherein the influencing of the cleaning program is selected from: a selection of a suitable cleaning program from a list of cleaning programs; a suggestion for a suitable cleaning program to a user of the cleaning and disinfecting apparatus; an influencing of at least one parameter of the cleaning program; a temperature of the cleaning fluid; an actuation of various nozzles; an application on the goods to be cleaned by nozzles which change in position; one or both of a prevention of the cleaning program or at least one subsequent cleaning program step of the cleaning program being carried out; an addition of at least one additional cleaning program step to the cleaning program; one or both of an output of at least one warning or at least one notification to a user.

10. The cleaning and disinfecting apparatus as claimed in claim 9, wherein the influencing of the cleaning program is an influencing of at least one parameter of the cleaning program, wherein the influencing of the cleaning program is an influencing of a parameter selected from the group consisting of a duration of at least one cleaning program step in the cleaning program, a change in at least one concentration of at least one component of the cleaning fluid.

11. The cleaning and disinfecting apparatus as claimed in claim 10, wherein the parameter is a change in at least one concentration of at least one component of the cleaning fluid, wherein the change in the at least one component of the cleaning fluid is one or both of a concentration of at least one cleaning agent and at least one disinfecting agent in the cleaning fluid.

12. The cleaning and disinfecting apparatus as claimed in claim 1, wherein the cleaning and disinfecting apparatus is further configured to carry out at least one learning program, wherein, in the learning program, at least one container with at least one known property is introduced into a visual range of the image detector by a user, wherein the property is identified by means of the image detector and an influencing of the cleaning program corresponding to the property can be specified by the user and can be stored in the cleaning and disinfecting apparatus.

13. The cleaning and disinfecting apparatus as claimed in claim 12, wherein, in the learning program, at least one container with at least one known property is introduced in a holder by a user.

14. The cleaning and disinfecting apparatus as claimed in claim 1, wherein the cleaning and disinfecting apparatus includes at least one process sensor in an interior of the cleaning chamber, wherein the process sensor is configured to identify a degree of soiling of the container, wherein the cleaning and disinfecting apparatus is configured to modify a sequence of the cleaning program in accordance with the identified degree of soiling.

15. The cleaning and disinfecting apparatus as claimed in claim 14, wherein the process sensor is an optical process sensor.

16. The cleaning and disinfecting apparatus as claimed in claim 14, wherein the cleaning and disinfecting apparatus is configured to modify one or both of a composition of the cleaning program or at least one parameter of at least one cleaning program step of the cleaning program, in accordance with the identified degree of soiling.

17. The cleaning and disinfecting apparatus as claimed in claim 1, wherein the cleaning and disinfecting apparatus is further configured to identify at least one cleaning result by means of the image detector after carrying out the cleaning program.

18. The cleaning and disinfecting apparatus as claimed in claim 1, wherein the cleaning and disinfecting apparatus has at least one warning device for outputting at least one warning to a user.

19. The cleaning and disinfecting apparatus as claimed in claim 1, wherein the cleaning and disinfecting apparatus is configured to identify, by means of the image detector, when at least one object is in a danger area of the cleaning and disinfecting apparatus.

20. A method for treating at least one container for human excretions, by using a cleaning and disinfecting apparatus as claimed in claim 1, the method comprising the following steps:
  emptying the container;
  applying cleaning fluid to the container that is positioned in the cleaning chamber;
  identifying at least one property of the container with the image detector; and
  influencing the cleaning program in accordance with the identified property.

21. The method as claimed in claim 20, wherein at least one image of the container is recorded by means of the image detector.

22. The method for treating at least one container for human excretions as claimed in claim 20, wherein the container is emptied during the cleaning program within the cleaning chamber.

* * * * *